United States Patent [19]
Berlin et al.

[11] Patent Number: 4,826,984
[45] Date of Patent: May 2, 1989

[54] HETEROAROTINOID COMPOUNDS AS ANTICANCER AGENTS

[75] Inventors: Kenneth D. Berlin; Elizabeth M. Holt; Warren T. Ford; Mark D. Thompson, all of Stillwater, Okla.

[73] Assignee: The Board of Regents for the Oklahoma Agricultural and Mechanical College acting for and on behalf of Oklahoma State University, Okla.

[21] Appl. No.: 9,083

[22] Filed: Jan. 27, 1987

Related U.S. Application Data

[63] Continuation-in-part of Ser. No. 598,482, Apr. 9, 1984, abandoned.

[51] Int. Cl.$^4$ ............... C07D 307/79; C07D 311/74; C07D 333/54; C07D 209/08
[52] U.S. Cl. ..................... 546/134; 548/469; 549/23; 549/58; 549/407; 549/462; 556/406
[58] Field of Search ............. 546/134; 548/469; 549/23, 58, 407, 462; 556/406

[56] References Cited

FOREIGN PATENT DOCUMENTS 2119801 11/1983 United Kingdom ............... 549/23

OTHER PUBLICATIONS

Lovey et al, J. Med. Chem., 1982, 25, pp. 71–75.
Dawson et al, J. Med. Chem, 1983, 26, pp. 1282–1293.
Pawson et al, J. Med. Chem, 1982, 25, pp. 1269–1277.

Primary Examiner—Mary C. Lee
Assistant Examiner—Mary Sue Howard
Attorney, Agent, or Firm—Head & Johnson

[57] ABSTRACT

Novel heteroarotinoid compositions characterized by the formulae:

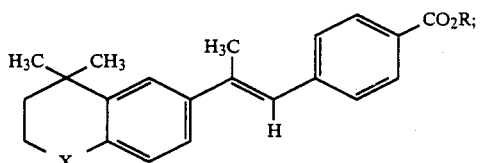

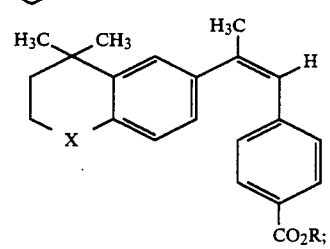

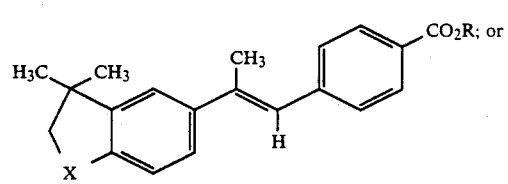

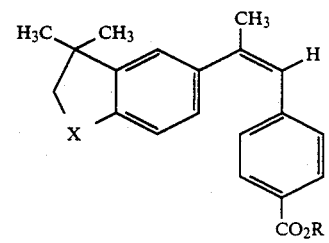

where R is H, $CH_3$ or $C_2H_5$ and X is S, S O, O, $NCH_3$, $Si(CH_3)_2$, $N^+(H)CH_3[Cl^-]$, $N^+(H)CH_3[Br^-]$ or $N^+(alkyl)$ $CH_3[Cl^-$ or $Br^-)$ where alkyl is $CH_3$, $C_2H_5$, $CH_2=CHCH_2$ or $C_6H_5CH_2$. Such compositions exhibit activity as anticancer agents.

13 Claims, No Drawings

HETEROAROTINOID COMPOUNDS AS ANTICANCER AGENTS

This is a continuation-in-part of co-pending application Ser. No. 598,482 filed on Apr. 9, 1984, now abandoned.

BACKGROUND OF THE INVENTION

1. Field of the Invention

This invention relates to anticancer compositions. More specifically, the invention relates to certain 4-[3,4-dihydro-4,4-dimethyl-2H-1-benzoheterapyran-6-yl)-1-propenyl]benzoates and derivatives thereof.

2. Description of the Prior Art

To the best knowledge of the inventors, the title compounds have not been reported in the literature but certain hydrocarbon counterparts are documented. Such hydrocarbon systems have been referred to as arotinoids and several papers on the subject have been published, such as in the *European Journal of Medicinal Chemistry*, 1980, Vol. 15, pages 9-15, entitled "Arotinoids, A New Class of Highly Active Retinoids" by P. Loeliger, W. Bollag and H. Mayer. Synthesis and stereochemistry are discussed. A second more recent publication has peripherally related derivatives and is entitled "Fluorinated Retinoic Acids and Their Analogues". 3. Synthesis and Biological Acitivity of Aromatic 6-Fluoro Analogues" by A. J. Lovey and B. A. Pawson. The article appeared in the *Journal of Medicinal Chemistry*, Vol. 25, pages 71-75 (1982). A review of the entire area of biological activity of retinoids and related compounds has been published in the *Journal of Medicinal Chemistry*, Vol. 25, pages 1269-1277 (1982). The title is "Retinoids at the Threshold: Their Biological Significance and Therapeutic Potential", by B. A. Pawson, C. W. Ehmann, L. M. Itri, and M. I. Sherman. The first paper contains work which is the most closely related to the compounds cited in this application in terms of preparation from ketones and conversion to the final product through a type of Wittig reaction. In no case, however, was a heteroatom ever involved in the ring systems employed and it is felt that the presence of the heteroatom makes a significant difference in the properties of the heteroarotinoids described and claimed herein.

According to the existing literature, some derivatives of the arotinoids have been found to possess useful biological activities. One type of test for therapeutic potency is the antipapilloma test (cited in the first article above) and the tracheal organ culture assay which is described in an article in the *Journal of Cancer Research*, Vol. 40, 3413-3425 (1980) by D. L. Newton, W. R. Henderson, and M. B. Sporn. The assays assess the ability of the test compound to prevent skin papillomas and carcinomas in mice or to prevent keratinization of cultured tracheal cells which frequently occurs when cells become premalignant. Further evidence on these points can be found in articles in entitled "Chemoprevention of Cancer with Retinoids" by M. B. Sporn and D. L. Newton, published in the *Federation Proceedings*, Vol. 38, pages 2528-2534 (1979) and "Structure-Activity Relationships of Retinoids in Hamster Tracheal Organ Culture" by D. L. Newton, W. R. Henderson, and M. B. Sporn, published in *Cancer Research*, Vol. 40, pages 3414-3425 (1980). Another test for potential anticancer activity of retinoic acid derivatives has been the ornithine decarboxylase assay which has been reviewed recently in connection with an evaluation of some aromatic retinoic acid compounds. The article is entitled "Aromatic Retinoic Acid Analogues. 2. Synthesis and Pharmacological Activity" by M. I. Dawson, R. Chan, P. D. Hobbs, W. Chao, and L. J. Schiff and was published in the *Journal of Medicinal Chemistry*, Vol. 26, pages 1282-1293 (1983). The compounds of the present inventions were assayed using the tracheal organ culture procedure.

The present invention novel (E)- and [(Z)]-4-[2-(3,4-dihydro-4,4-dimethyl-2H-1-benzoheterapyran-6-yl)-1-propenyl]benzoate and derivative compositions characterized by the formulae:

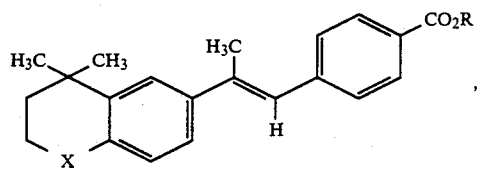

and

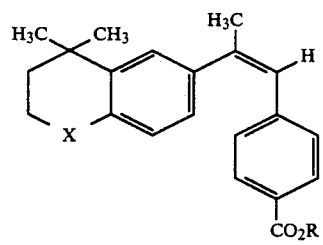

where R is H, CH$_3$, or C$_2$H$_5$ and where X is S,S→O,O,-N—CH$_3$, Si(CH$_3$)$_2$, N$^+$(H)CH$_3$[Cl$^-$], N$^+$(H)CH$_3$[Br$^-$], N$^+$(alkyl)CH$_3$[Br$^-$] and where alkyl is CH$_3$, C$_2$H$_5$, CH$_2$=CHCH$_2$, or C$_6$H$_5$CH$_2$; and the corresponding five-membered ring systems characterized by the formula:

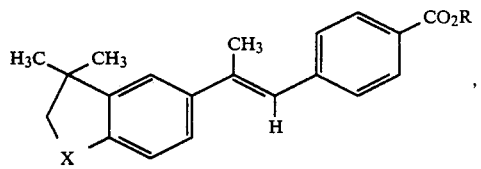

and

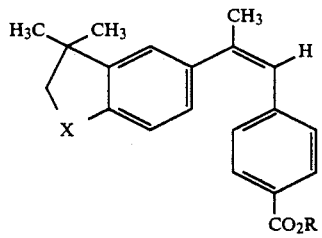

where R is H, CH$_3$, or C$_2$H$_5$ and where X is S,S→O,O,N,—CH$_3$, Si(CH$_3$)$_2$, N$^+$(H)CH$_3$(Cl$^-$] or N$^+$(H)CH$_3$[Br$^-$] or N$^-$(H)CH$_3$[Cl$^-$], N$^+$(H)CH$_3$[Br$^-$], N$^+$(alkyl)CH$_3$[Cl$^-$] or N$^+$(alkyl)CH$_3$[Br$^-$] and where alkyl is CH$_3$, C$_2$H$_5$, CH$_2$=CHCH$_2$ or C$_6$H$_5$CH$_2$.

It is an object of the present invention to provide novel heteroarotinoids which are structurally related to all trans-retinoic acid and which act as anticancer agents for the treatment of skin disorders and tumors. Fulfillment of this object and the presence and fulfillment of other objects will be apparent upon complete reading of the specification and claims.

DETAILED DESCRIPTION OF THE PREFERRED EMBODIMENT

The novel heteroarotinoid compositions according to the preferred embodiments of the present invention are heteronuclear rings, organic compounds based upon the generic structures designated below as compounds (1), (2), (3) and (4). The 1-position is occupied by the heteroatom such as O,S,S→O,N-alkyl or Si(CH$_3$)$_2$ (for purposes of this invention the heteroatom is symbolized by X in the formulae). The R symbolizes a —H, methyl or ethyl group. These heteroarotinoids are structurally related to all trans-retinoic acid which in turn is known to possess certain anticancer properties; however, they are structurally unique in that they possess a heteroatom. As exemplified later, the compositions of the present invention exhibit good activity with respect to the reversal of keratinization in the tracheal organ culture assay when compared with the standard all trans-retinoic acid. Furthermore, they appear to be less toxic than the standard.

PRODUCTS

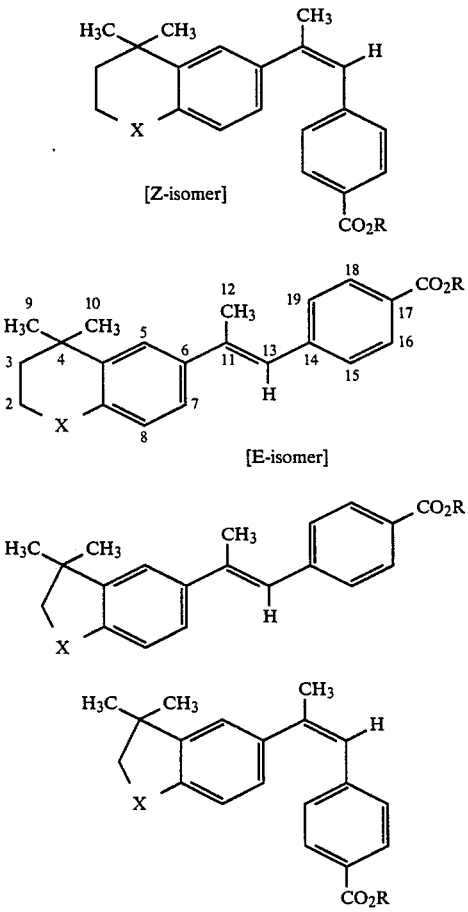

The new methodology and synthesis of the present invention permits the introduction of selected heteroatoms as replacements for methylene groups within the basic retinoic acid structure. Moreover, it is also possible according to the present invention to replace part of the backbone of the retinoic acid skeletal chain with a phenyl group. In addition, the present invention has been able to block or retard oxidation of the ring double bond in retinoic acid by the introduction of an aryl group. Also, the heteroatom has, advantageously, replaced the methylene group at the C(4) position of the retinoic acid structure which is known to undergo oxidation, via metabolic degradation in cell lines. As mentioned above and as exemplified later, preliminary toxicity data indicate that the tracheal cell lines (screening profile using cell culture lines from hamsters with all trans-retinoic acid as the standard) do not slough off as has been experienced with more toxic agents. Thus, it is felt that the reduced toxicity effects being observed in the heteroarotinoids of the present invention can be attributed, in part, to the presence of the heteroatom and perhaps this in turn can be explained or rationalized, at least in part, by the enhanced polar character and reduced lipophlicity relative to all trans-retinoic acid associated with the presence heteroatom. The presence of the heteroatom should also markedly improve the water solubility of the heteroarotinoids and improved drug transport. Thus the compositions according to the present invention are potential drugs for use particularly in the treatment of skin disorders of a cancerous nature.

Typically, the compounds according to the present invention are synthesized by one or the other of the following generalized reaction schemes which initially involve synthesis of key starting materials ketone 5 and ester-aldehyde 6 (underlined numerals as used herein correspond to numerically identified formulae). The remaining steps of the respective reaction schemes I and II involve the combining of reactants 5 and 6 to complete the overall synthesis of the desired heteroarotinoids 1, 2, 3, or 4 as previously shown. The respective reaction schemes I and II correspond to the synthesis of the "2H-1-benzoheterapyran-6-yl" and the corresponding "2H-1-benzoheterafuran" structures, respectively. The formation of the heterocyclic ketone 5 and the corresponding five-membered heterocyclic ketone 18 is felt to be crucial and novel in that no counterpart to the illustrated synthetic routes could be found in the chemical literature.

REACTANTS

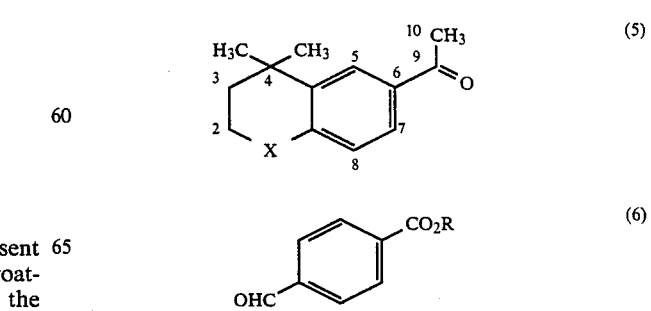

REACTION SCHEME I
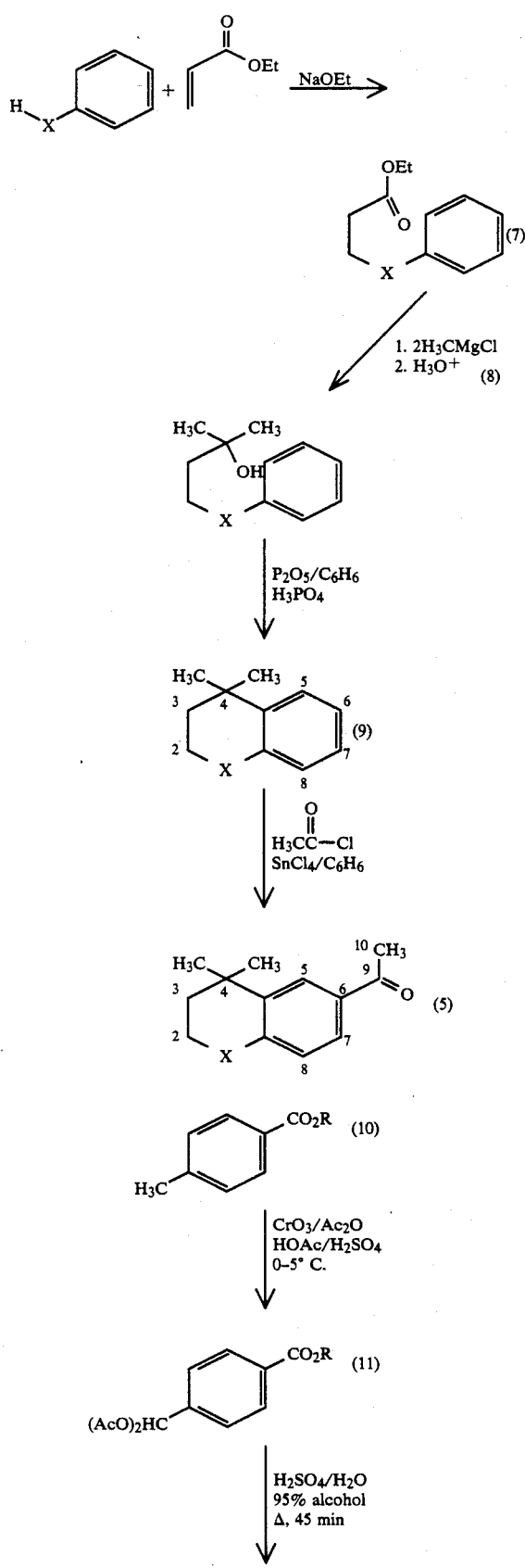
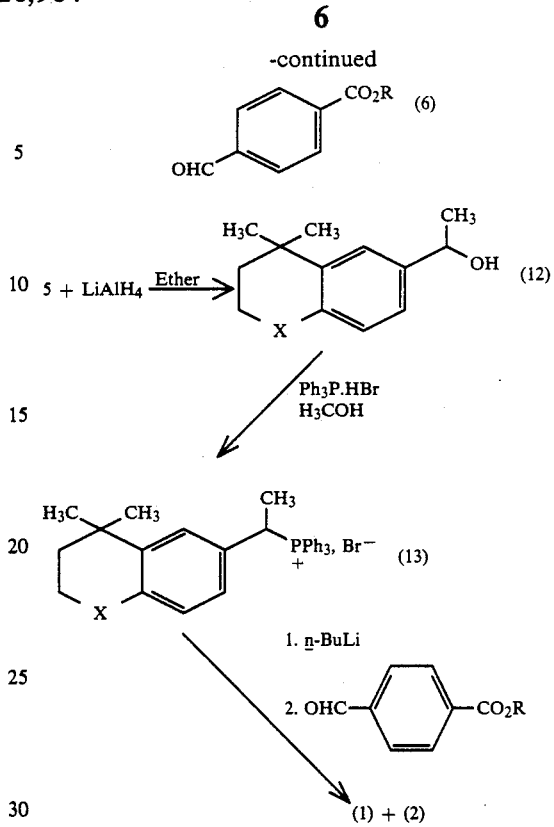
REACTION SCHEME II
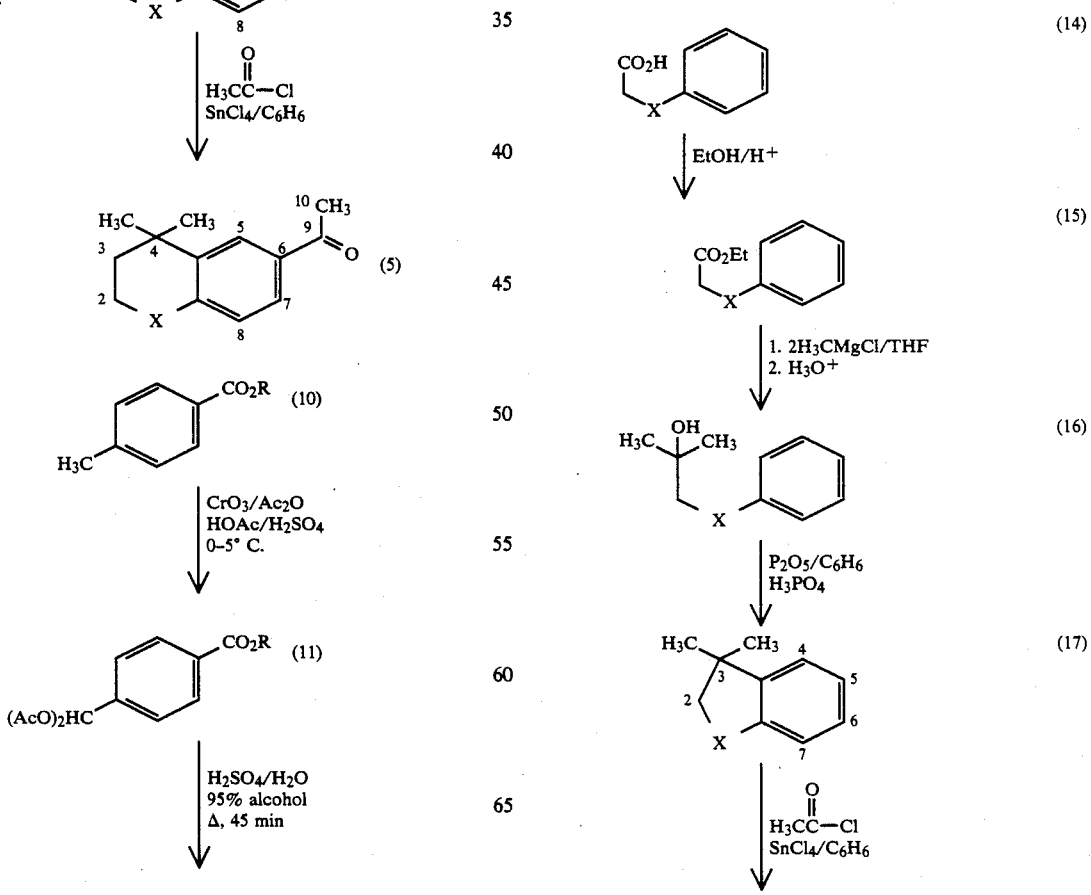

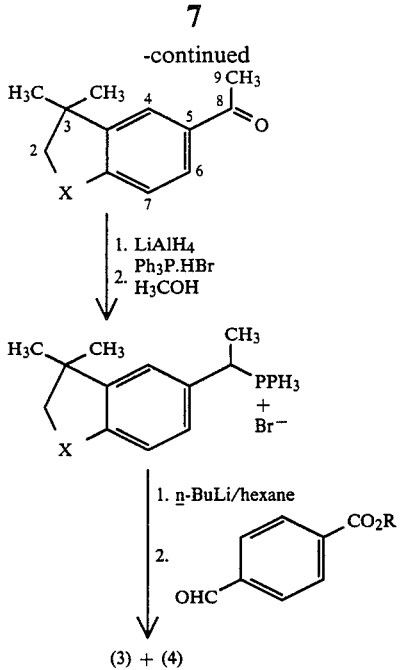

In order to further illustrate the general synthesis of the heteroarotinoids according to the present invention; their respective preparation and isolation as a purified biologically active heterocycle; and their activity in the tracheal organ assay, the following sequence of examples was performed.

EXAMPLE 1

Prepartion of Ethyl 3-(Phenylthio)propionate (7) (X=S)

Freshly distilled ethyl acrylate (75 mL) was added dropwise under $N_2$ to a stirred, ice-cold mixture of thiophenol (31.5 g, 0.286 mol) and sodium ethoxide (1.0 g). The ice bath was removed, and the mixture was stirred at room temperature for 24 hours. The mixture was diluted with ether (30 mL) and filtered. The ether and and excess ethyl acrylate were removed (vacuum). Vacuum distillation gave 49.6 g (82.6%) of compound 7 as a colorless liquid: bp 115°-118° C./0.2 mm (literature reports 117° C./2.5 mm; see K. Iwai, H. Kosugi, A. Miyazaki, and H. Uda, *Synthetic Communications,* 6, 357 (1976); IR (neat) 1730-1750 cm$^{-1}$ (C=O); $^1$H NMR (DCCl$_3$)δ1.22 (t, 3H, OCH$_2$CH$_3$), 2.58 (t, 2H, CH$_2$CO$_2$C$_2$H$_5$) 3.14 (t, 2H, SCH$_2$), 4.1 (q, 2H, OCH$_2$CH$_3$), 7.07-7.37 (m, 5H, Ar—H); $^{13}$C NMR (DCCl$_3$) ppm 14.2 [OCH$_2$CH$_3$], [SCH$_2$], 34.4 [CH$_2$CO$_2$], 60.5 [OCH$_2$CH$_3$]; Ar—C [126.3, 128.8, 129.8, 135.2 ], 171.3 [C=O].

Both hydrogen and carbon-13 NMR spectral shifts were measured from tetramethylsilane (TMS) standard on a Varian XL-100(15) or XL-300 spectrometer confirming the correct hydrogen distribution and carbon atom assignments.

2-Methyl-4-(phenylthio)-2-butanol (8) (X=S)

A solution of ethyl 3-(phenylthio)propionate (compound 7above; 20.0 g, 0.095 mol) in dry ether (5 mL) was added under $N_2$ to a stirred solution of methylmagnesium chloride in THF (2.9M, 105 mL, 0.304 mol) at a rate such that the solution boiled. The solution was then heated at reflux for an additional 36 hours. The mixture was cooled to room temperature and quenched with saturated aqueous NH$_4$Cl. The supernant liquid was decanted, and the residue was washed with dry ether (3×50 mL). The combined organics were dried (Na$_2$SO$_4$), and the ether was removed (vacuum). Vacuum distillation of the crude oil gave 14.95 g (80.3%) compound 8 as a colorless liquid: bp 93°-98° C./0.01 mm (literature reports 110°-113° C./0.7 mm, see F. Montanari, R. Daniel, H. Hogeveen, and G. Maccagnani, *Tetrahedron Letters,* 2685 (1964); IR (neat) 3200-3600 cm$^{-1}$ (OH); $^1$H NMR (DCCl$_3$)δ1.17 [s, 6H, (CH$_3$)$_2$], 1.66-1.84 [m, 2H, ArSCH$_2$CH$_2$], 2.38-2.47 [br s, 1H, OH], 2.88-305 [m, 2H, ArSCH$_2$], 7.04-7.34 [m, 5H, Ar—H]; $^{13}$C NMR (DCCl$_3$) ppm 28.2 [SCH$_2$], 28.9 [CH$_3$], 42.4 [SCH$_2$CH$_2$], 70.2 [C—OH]; Ar—C [125.3, 128.2, 128.4, 136.1].

4,4-Dimethylthiochroman or 3,4-Dihydro-4,4-dimethyl-2H-1benzothiopyran (9) (X=S)

A mixture of 2-methyl-4-(phenylthio)-2-butanol (compound 8 above, 10.0 g, 0.051 mol), H$_3$PO$_4$ (85%, 5 mL) and benzene (50 mL) were heated to reflux under $N_2$ with vigorous stirring for 24 hours. During this period, P$_2$O$_5$ (3×6.0 g, 0.126 mol) was added in three equal portions at 6 to 8 hour intervals. After cooling, the solution was decanted from the reddish-purple residue, and the residue was washed with ether (2×25 ML). The combined orgaics were washed with 5% aqueous NaHCO$_3$ (2×50 mL) and saturated aqueous NaCl (3×50 mL). After drying (Na$_2$SO$_4$) the solution, the solvent was removed, and the residual oil was vacuum distilled to give 7.4 g (81.5%) of compound 9 as a colorless liquid: bp 80°-85° C./0.01 mm; $^1$H NMR (DCCl$_3$) δ1.29 [s, 6H, (CH$_3$)$_2$], 1.84-1.97 [m, 2H, H(3)], 2.91-3.03 [m, 2H, H(2)], 6.9-7.35 [m, 4H, Ar—H]; $^{13}$C NMR (DCCl$_3$) ppm 23.1 [SCH$_2$], 30.2 [CH$_3$], 32.9 [(CH$_3$)$_2$C], 37.7 [SCH$_2$CH$_2$]; Ar—C [123.8, 125.8, 126.26, 126.3, 131.5 [C(4a)], 141.7 [C(8a)]].

4,4-Dimethylthiochroman-6-yl Methyl Ketone or 1-(3,4-Dihydro-4,4-dimethyl-2H-1-benzothiopyran-6-yl)ethanone (5) (X=S)

Stannic chloride (4.7 mL, 0.050 mol) was added dropwise under $N_2$ to a stirred solution of 4,4-dimenthylthiochroman (compound 9 above; 6.6 g, 0.037 mol) and acetyl chloride (3.1 g, 0.039 mol) in dry, thiophene-free benzene (30 mL). The resulting dark green solution was stirred at room temperature for 5 hours and then diluted with water (30 mL) and concentrated HCl (15 mL). The resulting mixture was heated to just below the boiling point for 15 minutes. The mixture was allowed to cool to room temperature, and the two layers were separated. The aqueous layer was extracted with benzene (5×20 mL), 5% aqueous Na$_2$CO$_3$ (2×40 mL), H$_2$O (50 mL), and brine (60 mL). After drying (Na$_2$SO$_4$) the solution, the solvent was removed (vacuum) leaving a viscous brown oil. Vacuum distillation gave 4.92 g (60.4%) of compound 5 as a pale yellow oil: bp 126°-130° C./0.02 mm; IR (neat) 1675-1685 cm$^{-1}$ (C=O); $^1$H NMR (DCCl$_3$)δ1.32 [s, 6H, (CH$_3$)$_2$], 1.84-1.97 [m, 2H, H(3)], 2.51 [s, 3H, CH$_3$C=O], 2.95-3.07 [m, 2H, H(2)], 7.07 [d, 1H, J=8 Hz, H(8)], 7.35 [dd, 1H, J=2 Hz, J=8 Hz, H(7)], 7.95 [d, 1H, J=2 Hz, H(5)]; $^{13}$C NMR (DCCl$_3$) ppm 23.1 [SCH$_2$], 26.2 [H$_3$CC=O], 29.7 [C(CH$_3$)$_2$], 32.9 [(CH$_3$)$_2$C], 36.8 [SCH$_2$CH$_2$]; Ar—C [125.7, 126.1, 132.8, 139.3, 141.6], 196.7 [C=O]; Mass spectral data for compound 5;

$C_{13}H_{16}OS$: m/e (M+) 220.0922 theoretical; Found: 220.0922.

Ethyl 4-Formylbenzoate (6)

A solution of ethyl p-toluate (compound 10; 6.0 g, 0.037 mol; prepared from p-toluic acid and ethanol by conventional techniques), glacial acetic acid (57 mL), and acetic anhydride (57 mL) in a flask equipped with a thermometer and a mechanical stirrer was cooled to 0° to 5° C. in an ice-salt bath. Concentrated $H_2SO_4$ (8.5 mL) was added slowly to the stirred solution. Chromium trioxide (10.0 g, 0.10 mol) was added in small portions over a period of 25 minutes. The temperature of the mixture was maintained below 5° C. at all times. After stirring at 0° to 5° C. for an additional 20 minutes, the mixture was poured into a breaker (⅜ full) with ice. Cold water was then added to bring the total volume to 600 mL. The resulting dark green-brown mixture was extracted with ether (3×250 mL), and the organic layers were combined. The organic layer was washed with water (3×200 mL), 5% aqueous $Na_2CO_3$ (2×200 mL), and brine (200 mL). After drying ($Na_2SO_4$) the solution, the solvent was removed leaving the diacetate 11 as a pale yellow liquid. A mixture of the crude diacetate 11, concentrated $H_2SO_4$ (2 mL), water (20 mL), and 95% ethanol (20 mL) was heated at reflux under $N_2$ for 45 minutes. The solution was allowed to cool to room temperature. After diluting the solution with water (40 mL), the resulting mixture extracted with ether (3×40 mL). The combined organic layers were washed with 5% aqueous $NaHCO_3$ (2×50 mL) and water (50 mL). After drying ($Na_2SO_4$) the solution, the solvent was removed leaving a yellow liquid. Vacuum distillation gave 3.1 g (47.1%) of compound 6 as a colorless liquid: bp 80°–84° C./0.05 mm (literature reports 142° C./13 mm; see K. H. Slotta and R. Kethur, Ber. 71, 335 [1938]); IR (neat) 1705–1735 cm$^{-1}$ (C=O); $^1$H NMR ($DCCl_3$) δ1.42 [t, 3H, $OCH_2CH_3$], 4.41 [q, 2H, $OCH_2CH_3$], 7.87–8.22 [pseudo q, 4H, Ar—H], 10.08 [br s, 1H, CHO]; $^{13}$C NMR ($DCCl_3$) ppm 14.2 [$OCH_2CH_3$], 61.4 [$OCH_2CH_3$]; Ar—C [129.2, 129.9, 135.2, 138.9], 165.2 [$CO_2C_2H_5$], 191.2 (CHO).

δ,4,4-Trimethylthiochroman-6-methanol or 3,3-Dihydro-δ,4,4-trimethyl-2H-1-benzothiopyran-6-methanol (12) (X=S)

A solution of 4,4-dimethylthiochroman-6-yl methyl ketone (compound 5 above; 4.0 g, 0.018 mol) in dry ether (20 mL) was added dropwise under $N_2$ to a stirred suspension of $LiAlH_4$ (1.0 g, 0.026 mol) in ether (75 mL). The resulting mixture was heated at reflux for 24 hours. Ethyl acetate was then added dropwise to destroy the excess $LiAlH_4$. A solution of 5% HCl (50 mL) was added, and the mixture was stirred for 10 minutes. The layers were separated, and the aqueous layer was extracted with ether (2×30 mL). The combined organic layers were washed with 5% aqueous $Na_2CO_3$ (2×50 mL) and brine (2×50 mL). After drying ($Na_2SO_4$) the solution, the solvent was removed leaving 3.8 g (95%) of compound 12 as a colorless oil. Crystallization (hex ne) with cooling to 0° C. gave a white granular powder: IR (melt) 3120–3640 cm$^{-1}$ (OH); –H NMR ($DCCl_3$)δ1.3 [s, 6H, $(CH_3)_2$], 1.39 [d, 3H, $H_3$ CHOH], 1.84–2.0 [m, 2H, $SCH_2CH_2$], 2.74–2.86 [br s, 1H, OH], 2.9–3.06 [m, 2H, $SCH_2$] 4.71 [q, 1H, $CH_3CHOH$], 6.94–7.02 [m, 2H, Ar—H], 7.30–7.36 [m, 1H, Ar—H]; $^{13}$C NMR ($DCCl_3$) ppm 23.0 [$SCH_2$], 25.0 [$H_3CCOH$], 30.2 [$(H_3C)_2C$], 33.1 [$(H_3C)_2C$], 37.7 [$SCH_2CH_2$], 70.2 [C(9)], 123.2, 123.6, 126.6, 130.7, 141.6, 142.9. The material was used without further purification.

[1-(4,4-Dimethylthiochroman-6-yl)ethyl]triphenylphosphonium Bromide or [1-(3,4-dihydro-4,4-dimethyl-2H-1-benzothiopyran-6-yl)ethyl]triphenylphosphonium Bromide (13) (X=S)

A solution of the alcohol 12 (0.5 g, 2.25 mmol) and triphenylphosphine hydrobromide (0.78 g, 2.27 mmol) in $CH_3OH$ (20 mL) was stirred at room temperature under $N_2$ for 26 hours. Removal of the solvent left a yellow oil which solidified after repeated trituration with dry ether. The resulting powder was stirred in dry ether (30 mL) for 8 hours, filtered, and dried (110° C./2 mm) to give 0.9 g (73.1%) of compound 13 as a tan powder; mp 139°–145° C. (dec); $^1$H NMR ($DCCl_3$) 1.07 [s, 3H, $CH_3$], 1.15 [s, 3H, $CH_3$], 1.75 [d, 3H, $CHCH_3$], 1.80–1.88 [m, 2H, H(3)], 2.96–3.02 [m, 2H, H(2)], 6.40–6.55 [m, 1H, $CHP(C_6H_5)_3$], 6.58 [dd, 1H, H(7)], 6.86 [d, 1H, H(8)], 7.45 [br s, 1H, H(5)], 7.62–7.90 [m, 15H, P+$(C_6H_5)_3$]. The salt was used without further purification.

Ethyl (E)-p-[2-(4,4-Dimethylthiochroman-6-yl)propenyl]benzoate or Ethyl (E)-4-[2-(3,4-dihydro-4,4-dimethyl-2H-1-benzothiopyran-6-yl)-1-propenyl]benzoate (X=S)

A solution of n-butyllithium in hexane (1.55M, 1.3 mL, 2.01 mmol) was added dropwise under $N_2$ to a stirred suspension of the phosphonium salt 13 (1.1 g, 2.01 mmol) in dry ether (30 mL). The resulting dark red mixture was stirred for 5 minutes. A solution of the freshly distilled aldehyde 6 (9.40 g, 2.25 mmol) in dry ether (15 mL) was then added all at once. The mixture became creamy yellow and then cream-colored, and a large amount of off-white solid precipitated. After stirring at room temperature for 36 hours, the mixture was filtered. The solid was washed with ether (50 mL). The combined filtrates were concentrated to give a yellow oil which was dissolved in warm 95% ethanol (50 mL). The resulting solution was filtered and then concentrated to 10 mL. After cooling slowly to room temperature, the resulting solid was filtered and washed with cold 95% ethanol. After drying in the air, 0.30 g (40.7%) of the compound (X=S) was obtained as a white solid: mp 92°–93° C.; IR (KBr) 1710–1725 cm$^{-1}$ (C=O); $^1$H NMR ($DCCl_3$) δ1.38 [s, 6H, $(CH_3)_2$], 1.41 [t, 3H, $OCH_2CH_3$], 1.96–2.02 [m, 2H, $SCH_2CH_2$], 2.28 [s, 3H, CH=C—$CH_3$], 3.04–3.09 [m, 2H, $SCH_2$], 4.4 [q, 2H, $OCH_2$], 6.82 [s, 1H, C=CH], 7.11 [d, 1H, J=9 Hz, H(8)], 7.21–7.28 [m, 1H, H(7)], 7.44 [d, 2H, Ar—H], 7.54 [s, 1H, H(5)], 8.07 [d, 2H, Ar—H]; Mass spectral data for $C_{23}H_{26}O_2S$: m/e (M+) theoretical 366.1653; Found: 366.1650.

EXAMPLE II

Ethyl (E)-p-[2-(4,4-Dimethylthiochroman-1-oxo-6-yl)propenyl]benzoate or Ethyl (E)-4-[2-(3,4-Dihydro-4,4-dimethyl-2H-1-benzothiopyran-1-oxo-6-yl)-1-propenyl]benzoate (X=S→O)

A solution of $NaIO_4$ (0.14 g, 0.65 mmol) in $H_2O$ (1 mL) was added in one portion under $N_2$ to a stirred suspension of the compound of Example I (X=S) (0.118 g, 0.322 mmol) in methanol (10 mL). The mixture was stirred at room temperature for an additional 36 hours.

A large amount of white solid precipitated during this time. The mixture was concentrated. The residue was dissolved in HCCl$_3$ (20 mL) and then filtered and concentrated. The resulting oil was triturated with cold hexane to induce crystallization. Recrystallization (hexane) gave 55 mg (44.7%) of the compound (X=S→O) as a white powder: mp 91°-93° C.; IR (KBr) 1700-1715 (C=O), 1030-1040 cm$^{-1}$ (S→O); $^1$H NMR (DCCl$_3$) 1.37 [s, 3H, CH$_3$], 1.41 [t, 3H, OCH$_2$CH$_3$], 1.51 [s, 3H, CH$_3$], 1.84-1.94 [m, 1H H(3)], 2.30 [s, 3H, CH=C(CH$_3$)], 2.48-2.60 [m, 1H, H(3)], 3.08-3.23 [m, 2H, H(2)], 4.41 [q, 2H, OCH$_2$CH$_3$], 7.46 [d, 2H, Ar—H], 7.51 [dd, J=9 Hz, J=3 Hz, 1H, H(7)], 7.58 [d, J=3 Hz, 1H, H(5)], 7.77 [d, J=9 Hz, 1H, H(8)], 8.09 [d, 2H, Ar—H]; Mass spectral data for C$_{23}$H$_{26}$O$_3$S: m/e (M+) theoretical 382.1603; Found: 382.1595.

EXAMPLE III

Methyl 3-Phenoxypropionate

To demonstrate the methyl ester, as well as the ethyl ester, may be used to make members of composition 7, we illustrate the preparation of the corresponding methyl ester of composition 7 in which the Et group is replaced by Me and X is O. A solution of 3-phenoxypropionic acid (10.0 g, 0.060 mol) and p-toluenesulfonic acid (0.6 g, 0.0033 mol) in methanol (250 mL) was heated at reflux through 3 Å molecular sieve for 36 hours under N$_2$ in a flask equipped with a Soxhlet extractor and a condenser. The solution was allowed to cool to room temperature and then was concentrated to a volume of 50 mL, diluted with water (50 mL), and extracted with ether (2×75 mL). The combined organic layers were washed with 5% aqeuous NaHCO$_3$ (75 mL), H$_2$O (75 mL), and brine (75 mL). After drying (Na$_2$SO$_4$) the solution, the solvent was removed (vacuum). Vacuum distillation gave 9.45 grams (87.1%) of the title ester as a colorless liquid: by 85°-87° C./0.1 mm (literature reports 85° C./0.4 mm; see C. E. Rehberg and M. D. Dixon [J. Am. Chem. Soc. 72, 2205 [1972]): IR (neat) 1740-1750 cm$^{-1}$ (C=O); $^1$H NMR (DCCl$_3$) δ 2.78 [s, 2H, CH$_2$CO$_2$CH$_3$], 3.70 [s, 3H, OCH$_3$], 4.23 [2H, OCH], 6.84-7.02 and 7.18-7.35 [m, 5H, ArH]; $^{13}$C NMR (DCCl$_3$) ppm 34.3 [H$_2$CCO$_2$], 51.7 [CH$_3$], 63.2 [Ar—OCH$_2$]; Ar—C [114.5, 120.8, 129.2, 158.3, 171.1].

2-Methyl-4-phenoxy-2-butanol (8) [X=O]

A solution of methyl 3-phenoxypropionate (7.9 g, 0.038 mol) in dry ether (20 mL) was added dropwise under N$_2$ to a stirred solution of CH$_3$MgCl in THF (2.9M, 40.2 mL, 0.12 mol). The mixture was heated at reflux at 24 hours, allowed to cool to room temperature and quenched with saturated aqueous NH$_4$Cl. The supernatant liquid was decanted, and the residue was washed with dry ether (3×50 mL). The combined organic solutions were dried (Na$_2$SO$_4$), and the solvent was removed. Vacuum distillation gave 5.35 g (76.4%) of compound 8 (X=O) as a colorless liquid: bp 81°-84° C./0.07 mm; IR (neat) 3140-3620 cm$^{-1}$ (OH); $^1$H NMR (DCCl$_3$) δ 1.26 [s, 6H, (CH$_3$)$_2$], 1.95 [t, 2H, ArOCH$_2$CH$_2$], 2.8-3.0 [br s, 1H, OH], 4.12 [t, 2H, ArOCH$_2$], 6.82-6.96 (m, 3H, Ar—H], 7.16-7.3 [m, 2H, Ar—H]; $^{13}$C NMR (DCCl$_3$) ppm 29.5 [CH$_3$], 41.6 [OCH$_2$CH$_2$], 64.9 [OCH$_2$], 70.3 [(H$_3$C)$_2$C]; Ar—C [114.3, 120.8, 129.3, 158.3].

4,4-Dimethylchroman or 3,4-Dihydro-4,4-dimethyl-2H-1-benzopyran (9) (X=O)

A solution of 2-methyl-4-phenoxy-2-butanol (8, X=O, 7.8 g, 0.043 mol) in nitromethane (50 mL) was added dropwise under N$_2$ to a stirred suspension of anhydrous AlCl$_3$ (7.8 g, 0.058 mol) in nitromethane (30 mL). After stirring at room temperature for an additional 24 hours, a solution of 6N HCl (80 mL) was added slowly. The resulting mixture was stirred for 10 minutes and diluted with ether (5 mL). The layers were separated, and the organic layer was washed with H$_2$O (50 mL), saturated aqueous NaHCO$_3$ (4×50 mL), H$_2$O (50 mL), and brine (4×50 mL). After drying (Na$_2$SO$_4$) the solution, the solvent was removed. Vacuum distillation of the resulting dark brown oil gave 4.35 g (62%) of compound 9 (X=O) as a colorless liquid: bp 74°-80° C./0.7 mm (literature reports 93+ C./10 mm; see J. Colonge, E. Le Sech, and R. Marey, Bull Soc. Chim. France, 776 (1957); $^1$H NMR (DCCl$_3$) δ 1.31 [s, 6H, (CH$_3$)$_2$], 1.80-1.84 [m, 3H, H(3)], 4.16-4.20 [m, 2H, H(2)], 6.78-7.29 [m, 4H, Ar—H]; $^{13}$C NMR (DCCl$_3$) ppm 30.5 [(H$_3$C)$_2$C], 31.1 [CH$_3$] 37.7 [OCH$_2$CH$_2$], 63.0 [OCH$_2$]; Ar—C [116.9, 120.4, 126.9, 131.6, 153.5].

4,4-Dimethylchroman-6-yl Methyl Ketone or 1-(3,4-Dihydro-4,4-dimethyl-2H-1-benzopyran-6-yl)ethanone (5) (X=O)

Anhydrous AlCl$_3$ (3.4 g, 0.025 mol) was added in small portions to a solution of 4,4-dimethylchroman (compound 9; (X=O), 4.0 g, 0.024 mol) and acetyl chloride (2.0 g, 0.025 mol) in CH$_3$NO$_2$ (35 mL) under N$_2$. After stirring at room temperature for 6 hours, 6N HCl (35 Ml) was added slowly, and the resulting mixture was stirred for 10 minutes. The mixture was diluted with ether (40 mL), and the layers were separated. The organic layer was washed with H$_2$O (40 mL), saturated aqueous NaHCO$_3$ (4×30 mL), H$_2$O (40 mL), and brine (2×40 mL). After drying (Na$_2$SO$_4$) the solution, the solvent was removed leaving a dark, reddish brown oil. Vacuum distillation gave 3.4 grams (67.5%) of compound 5 (X=O) as a pale yellow liquid: bp 108°-112° C./0.01 mm; IR (neat) 1675-1685 cm$^{-1}$ (C=O); $^1$H NMR (DCCl$_3$) δ 1.36 [s, 6H, (CH$_3$)$_2$C], 1.83-1.87 [m, 2H, H(3)], 2.55 [s, 3H, H$_3$CC=O], 4.24-4.28 [m, 2H, H(2)], 6.83 [d, J=9 Hz, 1H, H(8)], 7.71 [dd, J=9 Hz, J=3 Hz, 1H, H(7)], 7.98 [d, J=3 Hz, H(5)]; $^{13}$C NMR (DCCl$_3$) ppm 26.3 [CH$_3$], 30.6 [(H$_3$C)$_2$C], 37.0 [OCH$_2$CH$_2$], 63.4 [OCH$_2$], 116.9 [C(8)], 127.8, 128.16 [C(5), C(7)], 130.0, 131.6 [C(4a), C(6)], 158.0 [C(8a)]; Mass spectral data for C$_{13}$H$_{16}$O$_2$: m/e (M+) theoretical 204.1150; Found: 204.1153.

α,4,4-Trimethylchroman-6-methanol or 3,4-Dihydro-α,4,4-trimethyl-2H-1-benzopyran-6-methanol (12) (X=O)

A solution of the ketone 5 (X=O) (3.0 g, 0.015 mol) in anhydrous ether (15 mL) was added dropwise under N$_2$ to a stirred suspension of LiAlH$_4$ (0.8 g, 0.0211 mol) in dry ether (50 mL). The mixture was heated at reflux for 24 hours. After cooling to room temperature, ethyl acetate was added dropwise to destroy the excess LiAlH$_4$. A solution of 5% HCl (50 mL) was then added, and the resulting mixture was stirred for 5 minutes. The layers were separated, and the aqueous layer was washed with ether (2×50 mL). The combined organic layers were washed with 5% aqueous Na$_2$CO$_3$ (2×50 mL) and brine (2×50 mL). After drying (Na$_2$SO$_4$) the solution, the solvent was removed leaving a yellow oil which solidified after scratching. Recrystallization (hexane) gave 1.8 g (59.4%) of compound 12 (X=O) as a white solid: mp 70°–71° C.; IR (KBr) 3140–3640 cm$^{-1}$ (OH); $^1$H NMR (DCCl$_3$) 1.31 [s, 6H, (CH$_3$)$_2$C], 1.43 [d, 3H, H$_3$CHOH], 1.74–1.83 [m, 2H, H(3)], 2.4–2.44 [s, 1H, OH], 4.10–4.18 [m, 2H, H(2)], 4.76 [q, 1H, CHOH], 6.76 [d, J=9 Hz, 1H, H(8)], 7.07 [dd, J=9 Hz, J=3 Hz, 1H, H(7)], 7.28 [d, J=3 Hz, 1H, H(5)]; $^{13}$C NMR (DCCl$_3$) ppm 25.0 [H$_3$CC=O], 30.6 [C(4)], 31.0 [(H$_3$C)$_2$C], 37.6 [C(3)], 63.0 [C(2)], 70.2 [C(9)], 116.9 [C(8)], 124.0, 124.3 [C(5), C(7)], 131.4, 137.7 [C(4)a, C(6)], 152.9 [C(8a)]; Mass spectral data for C$_{13}$H$_{18}$O$_2$: m/e (M$^+$) theoretical 206.1307; Found: 206.1308.

[1-(4,4-Dimethylchroman-6-yl)ethyl]triphenylphosphonium Bromide or
[1-(3,4-Dihydro-4,4-dimethyl-2H-1-benzopyran-6-yl)ethyl]triphenylphosphonium Bromide (13) (X=O)

A solution of the alcohol compound 12 (X=O) (0.70 g, 3.4 mmol) and triphenylphosphine hydrobromide (1.2 g, 3.5 mmol) in methanol (30 mL) was stirred under N$_2$ at room temperature for 24 hours. The solvent was removed (vacuum), and the resulting oil was triturated repeatedly with dry ether until it solidified. The white solid was stirred in dry ether (30 mL) at room temperature under N$_2$ for 4 hours, filtered, and dried (110° C./~2 mm) to give 1.45 g (80.3%) of compound 13 (X=O) as a white powder: mp 149°–155° C. (dec); $^1$H NMR (DCCl$_3$) δ 1.08 [s, 3H, CH$_3$], 1.14 [s, 3H, CH$_3$], 1.72–1.78 [m, 2H, H(3)], 1.83 [d, 3H, CHCH$_3$], 4.12–4.18 [m, 2H, H(2)], 6.2–6.32 [m, 1H, CHP$^+$Ph$_3$, Br$^-$], 6.57 [d, 1H, H(8)], 6.67 [d, 1H, H(7)], 7.24 [br s 1H, H(5)], 7.63–7.84 [m, 15H, P$^+$(C$_6$H$_5$)$_3$]. The salt was used without further purification.

Ethyl
(E)-p[2-(4,4-Dimethylchroman-6-yl)propenyl]benzoate or Ethyl
(E)-4-[2-(3,4-Dihydro-4,4-dimethyl-2H-1-benzopyran-6-yl)-1-propenyl]benzoate (X=O)

A solution of n-butyllithium in hexane (1.55M, 2.13 mL, 3.30 mmol) was added dropwise under N$_2$ to a stirred suspension of the phosphonium salt 13 (X=O) (1.75 g, 3 mmol) in dry ether (30 mL). The resulting dark, reddish brown mixture was stirred at room temperature for 5 minutes. A solution of the aldehyde 6 (0.60 g, 3.37 mmol) in dry ether (15 mL) was then added. The mixture changed from reddish brown to creamy yellow, and a large amount of off-white solid precipitated. After stirring at room temperature for 36 hours, the mixture was filtered The resulting solid was washed with ether (75 mL), and the combined filtrates were concentrated to give a yellow oil. The oil was chromatographed through a column (8×200 mm) packed with neutral alumina (about 10 g). The product was eluted with 5% ether/hexane (250 mL). Concentration of the eluent gave a viscous oil which was dissolved in a minimum amount of boiling 95% ethanol. Cooling the solution to 0° C. and scratching gave 0.30 grams (26.0%) of the compound (X=O) as a white granular solid: mp 72.5°–73.5° C.; IR (KBr) 1710–1725 cm$^{-1}$ (C=O); $^1$H NMR (DCCl$_3$) δ 1.37 [s, 6H, (CH$_3$)$_2$C], 1.39 [t, 3H, OCH$_2$CH$_3$], 1.81–1.87 [m, 2H, H(3)], 2.27 [s, 3H, CH=C(CH$_3$)], 4.17–4.24 [m, 2H, H(2)], 4.38 [q, 2H, OCH$_2$CH$_3$], 6.77 [s, 1H, CH=C(CH$_3$)], 6.81 [d, J=9 Hz, 1H, H(8)], 7.26 [dd, J=9 Hz, J=3 Hz, 1H, H(7)], 7.41 [d, 2H, Ar—H], 7.44 [d, J=3 Hz, 1H, H(5)], 8.06 [d, 2H, Ar—H]; Mass spectral data for C$_{23}$H$_{26}$O$_3$: m/e (M$^+$) theoretical 350.1882; Found: 350.1884. The presence of the Z isomer in an oil obtained from the chromatography was indicated by the following $^1$H NMR signals: δ 2.76–2.81 [m, H(3)], 2.20 [s, 3H, Z CH=C(CH$_3$)], 4.16–4.20 [m, H(2)], 6.44 [br s, 1H, Z CH=C(CH$_3$)].

EXAMPLE IV

To demonstrate the ease with which the corresponding carboxylic acids might be obtained from the esters, the following synthesis of acid with X being O and R being H was performed.

(E)-p-[2-(4,4-Dimethylchroman-6-yl)propenyl]benzoic Acid or
(E)-4-[2-(3,4-Dihydro-4,4-dimethyl-2H-1-benzopyran-6-yl)-1-propenyl]benzoic Acid (X=O, R=H)

The heteroarotinoid (X=O, R=Et) (0.20 g, 0.57 mmol) was heated at reflux under N$_2$ for 4 hours in a solution of NaOH (0.1 g, 2.50 mmol) in 95% C$_2$H$_5$OH (2 mL) and H$_2$O (5 mL). After cooling slowly to room temperature, the solution was acidified (litmus) with concentrated HCl. The resulting white solid was filtered, washed with water, and air-dried. Recrystallization (95% ethanol) gave 0.135 grams (73.4%) of acid 1 (X=O, R=H) as a white solid: mp 183°–183.5° C.; IR (KBr) 2390–3320 (OH, CH), 1670–1695 cm$^{-1}$ (C=O); $^1$H NMR (DCCl$_3$) δ 1.38 [s, 6H, (CH$_3$)$_2$C], 1.84–1.9 [m, 2H, H(3)], 2.30 [s, 3H, CH=C(CH$_3$)], 4.21–4.26 [m, 2H, H(2)], 6.80 [s, 1H, CH=C(CH$_3$)], 6.83 [d, J=9 Hz, 1H, H(8)], 7.29 [dd, J=9 Hz, J=3 Hz, 1H, H(7)], 7.46 [d, J=3 Hz, 1H, H(5)], 7.48 [d, 2H, Ar—H], 8.15 [d, 2H, Ar—H]; Mass spectral data for C$_{21}$H$_{22}$O$_3$: m/e (M$^+$) theoretical 322.1569; Found: 322.1570.

EXAMPLE V

Since a modification was required to produce compound 9 (X=N—CH$_3$) from the general procedure, the following synthesis of the nitrogen analogue was performed.

Ethyl 3-phenylmethylaminopropionate (7) (X=N—CH$_3$)

A solution of freshly distilled N-methylaniline (267.5 g, 2.50 mol) and glacial acetic acid (50 mL) was placed in a one liter, 3-necked flask equipped with a water cooled condenser (carrying a CaCl$_2$ drying tube) and an addition funnel charged with ethyl acrylate (250 g, 2.50 mol). The flask was warmed on a steam bath and the ethyl acrylate was added dropwise over a 25 minute period. The resulting yellow solution was heated with occasional swirling for 17 hours during which time it turned deep red. This solution was washed with 5% NaHCO$_3$ (4×75 mL) and then with brine (3×75 mL). During the first wash, an emulsion formed, and 50 mL of diethyl ether was added to destroy it. After drying (MgSO$_4$) the solution, evaporation gave a red oil which was distilled to give 404.5 grams, (78.2%) of compound 7 (X=N—CH$_3$) as a yellow oil: bp 105°–109° C./0.2 mm (literature report 98°–100° C./0.05 mm; see D. W. Adamson, *J. Chem. Soc. (Supplement I)* S-144 (1949)): IR (neat) 1740 (C=O) cm$^{-1}$; $^1$H NMR (DCCl$_3$) δ 1.15 [t, 3H, OCH$_2$CH$_3$], 2.46 [t, 2H, CH$_2$CO$_2$CH$_3$, J=7.08 Hz], 2.80 [s, 3H, NCH$_3$], 3.59 [t, 2H, NCH$_2$, J=7.08 Hz], 4.04 [q, 2H, OCH$_2$CH$_3$], 6.67 [m, 3H, o & p—ArH], 7.18 [m, 2H, m—ArH]; $^{13}$C NMR (DCCl$_3$) ppm 14.1 [OCH$_2$CH$_3$], 31.6 [C(2)], 37.9 [C(4)], 48.4

[C(3)], 60.2 [OCH$_2$], 112.3 [C(6,10)], 116.5 [C(8)], 129.0 [C(7,9)], 148.4 [C(5)], 171.7 [C(1)]; Mass spectral data for C$_{12}$H$_{17}$NO$_2$: m/e (M+) 207.1259; Found: 207.1261.

2-Methyl-4-(phenylmethylamino)-2-butanol (8) (X=N—CH$_3$)

A solution of methylmagnesium chloride (Aldrich, 2.9M in THF, 414 mL, 1.20 mol) was placed in a one liter, 3-necked, round-bottom flask along with a magnetic stirring bar. The flask was equipped with a thermometer, a dry ice condenser carrying a CaCl$_2$ drying tube, and an additional funnel charged with ethyl 3-phenylmethylaminopropionate (compound 7; X=N—CH$_3$, 100 g, 0.483 mol). The apparatus was flushed with nitrogen and the flask and contents were cooled to −5° C. in an ice-salt bath. The ester 7 (X=N—CH$_3$) was added dropwise at such a rate that the temperature stayed below 15° C. (45 minutes). After warming slowly to room temperature, the solution was stirred for an additional 90 minutes. The mixture was poured onto 400 grams of crushed ice contained in a 2 liter Erlenmeyer flask, and then 85 mL of concentrated HCl was slowly added with stirring. Stirring was continued for 1 hour and then water was added to dissolve the precipitated salts which brought the total volume to 1400 mL. The solution was then neutralized by addition of solid K$_2$CO$_3$ (50 g). Two layers separated and the aqueous layer was extracted with HCCl$_3$ (3×100 mL). The combined organic portions were washed with brine (50 mL) and dried (K$_2$CO$_3$). Evaporation of the solvent gave an orange oil which was distilled under vacuum to give 74.7 g (80.1%) of compound 8 (X=N—CH$_3$) as a pale yellow liquid: bp 95°–99° C./0.08 mm; IR (neat) cm$^{-1}$ 3150–3650 cm$^{-1}$ (OH); $^1$H NMR (DCCl$_3$) δ 1.62 [s, 6H, HOC(CH$_3$)$_2$], 2.06 [t, 2H, J=7.82 Hz, NCH$_2$CH$_2$], 3.24 [s, 3H, NCH], 3.34 [s, 1H, OH], 3.81 [t, 2H, J=7.86 Hz, NCH$_2$], 7.15 [m, 3H, o & p—ArH], 7.64 [t, 2H, m—ArH]; $^{13}$C NMR (DCCl$_3$) ppm 29.3 [C(1,12)], 38.1 [C(11)], 38.5 (C(3)], 48.5 [C(4)], 69.8 [C(2)], 112.8 [C(6,10)], 116.4 [C(8)], 128.9 [(C(7,9)], 149.1 [C(5)]; Mass spectral data for C$_{12}$H$_{19}$NO: m/e (M+) 193.1467; Found: 193.1464.

1,4,4-Trimethyl-1,2,3,4-tetrahydroquinoline (9)(X=N—CH$_3$)

A solution of compound 8 (X=N—CH$_3$, 21.3 g, 0.110 mol) in CH$_2$Cl$_2$ (350 mL) was placed in a 500 mL, round-bottom flask equipped with a magnetic stirring bar. To this was added cautiously a solution of F$_3$CCO$_2$H (5 mL) in concentrated H$_2$SO$_4$ (50 mL). The mixture was boiled for 3 hours after which time the CH$_2$Cl$_2$ was evaporated. The residue was neutralized by the addition of a saturated aqueous solution of K$_2$CO$_3$. The resulting slurry was extracted with HCCl$_3$ (3×75 mL), and the combined extracts were washed with 5% NaHCO$_3$ (3×50 mL) and then with brine (2×50 mL). After drying (K$_2$CO$_3$), the solution gave a red oil which was distilled under vacuum to yield compound 9 (X=N—CH$_3$, 14.8 g, 77.1%) as a colorless oil: bp 137°–139° C./0.06 mm; $^1$H NMR (DCCl$_3$) δ1.24 [s, 6H, C(CH$_3$)$_2$], 1.69 [t, 2H, NCH$_2$CH$_2$, J=5.96 Hz], 2.79 [s, 3H, HCH$_3$], 3.11 [t, 2H, NCH$_2$, J=5.94 Hz], 6.51–7.14 [m, 4H, ArH]; $^{13}$C NMR (DCCl$_3$) ppm 31.0 [C(10,11)], 31.9 [C(4), 37.3 [C(3)], 39.2 [C(9)], 47.6 [C(2)], 131.2 [C(4a)], 145.3 [C(8a)]; Mass spectral data for C$_{12}$H$_{17}$N: m/e (M+(175.1361; Found: 175.1358. When the cyclization was attempted using P$_2$O$_5$ in C$_6$H$_6$/H$_3$PO$_4$, the yield of compound 9 (X=N—CH$_3$) was 55%.

EXAMPLE VI

An evaluation of the anticancer properties of the heteroarotinoids was made via the standard hamster tracheal organ culture bioassay (see D. L. Newton, W. R. Henderson, and M. B. Sporn in *Structure-Activity Relationships of Retinoids,* National Cancer Institute, Revised Edition, Feb. 26, 1980; and D. L. Newton, W. R. Henderson, and M. B. Sporn, *Cancer Research,* 40, 3413 [1980]). The assay involves the ability of a test compound in vitro to reverse keratinization in tracheal organ cultures obtained from vitamin A deficient hamsters. The relationship of vitamin A deficient epithelial tissues and precancerous lesions is well known (see C. E. Orfanos, *Retinoids-Advances in Basic Research and Therapy,* Springer-Verlag, New York, 1981). For example, the addition of retinoids can reverse the anaplastic epithelial lesions induced in prostate glands by chemical carcinogens (see D. P. Chopra and L. J. Wilkoff, *Proc. Am Assoc. Cancer Research,* 16, 35 (1975); and I. Lasnitzki, *British Journal of Cancer,* 9, 434 [1955]). The basic procedure for the bioassay involving the vitamin A deficient hamster tracheal organ culture is presented below with the results obtained for some of the compositions.

The harvested tracheas were cultured in a serum-free medium and were gassed with 50% O$_2$, 45% N$_2$, and 5% CO$_2$. The serum-free culture consists of CMRL Medium 1066 with crystalline bovine insulin (1.0 µg/mL), hydrocortisone hemisuccinate (0.1 µg/mL), glutamine (2 mM), pencillin (100 inits/mL), and streptomycin (100 µg/mL). The cultures were incubated for 3 days at 35°–36° C. After incubation in the retinoid-free medium, some of the tracheas were harvested. Most of the specimens had significant squamous metaplasia. The remaining cultures were divided into 3 groups. The first group was treated with the experimental heteroarotinoid in spectrograde dimethyl sulfoxide (DMSO) at concentrations of 10$^{-8}$M, 10$^{-9}$M, and 10$^{-10}$M (final concentration of DMSO in culture medium was 0.1%). The other groups were culture media without test heteroretinoid and culture media with the standard all trans-retinoic acid in DMSO at concentrations of 10$^{-10}$M, 10$^{-11}$M, and 10$^{-12}$M (all trans-retinoic acid has an ED$_{50}$ of 1×10$^{-11}$M). The all trans-retinoic acid was used with each culture because it is the most potent of natural occuring retinoids in reversing keratinization caused by vitamin A deficiency and is a good compound to determine if the assay is working correctly. A final culture was prepared with only DMSO present.

The culture medium was changed three times per week for 10 days. At the end of that time, all tracheas were harvested and fixed in a 4% (or sometimes 10%) formaldehyde-1% glutaraldehyde solution. The material was then embedded in paraffin and cross-sections of the tracheas were examined under a microscope for the presence of keratin or keratohyaline granules. A synthetic retinoid was judged as having good anticancer activity if neither keratin nor keratohyaline granules were present or if only keratohyaline granules were not present. If both were seen, the retinoid was considered inactive. The following Table contains the resulting test data which clearly demonstrates the activity of several of the compositions according to the present invention. The E compound (X=S, R=C$_2$H$_5$) showed very good activity and approximately one-half log unit less than the all trans-retinoic acid. Heteroartinoid E compound (X=O, R=C₂H₅) and the acid E compound (X=O, R=H) demonstrated good activity only one log unit less than the standard all trans-retinoic acid. The sulfoxide analogue (E compound wherein, X=S→O, R=C₂H₅) was less active but nevertheless displayed activity within the range of the standard. Since the compositions described within this application have heteroatoms which increase water solubility (and less lipid solubility), they appear to be less toxic than all trans-retinoic acid which is known to be acutely toxic in single large doses (see C. E. Orfanos, *Retinoids-Advances in Basic Research and Therapy*, Springer-Verlag, New York, 1981; and T. Moore, *Vitamin A*, Elsevier Publishing Company, New York, 1957). Sloughing of the cells in the culture studies was common with the toxic all trans-retinotic acid but was not observed with the heteroarotinoids in this work.

TABLE I

Activity of Compounds in the Hamster Tracheal Organ Culture Assay

| Aroretinoid | Concentration(M) | % Active | ED$_{50}$(M)$^a$ |
|---|---|---|---|
| trans-retinoic acid | 10$^{-10}$ | 76.9 | 2 × 10$^{-11}$ |
| | 10$^{-11}$ | 41.7 | |
| | 10$^{-12}$ | 23.1 | |
| 1 (X = S, R = C₂H₅) | 10$^{-9}$ | 100 | 6 × 10$^{-11}$ |
| | 10$^{-10}$ | 53.8 | |
| | 10$^{-11}$ | 28.6 | |
| | 10$^{-12}$ | 33.7 | |
| trans-retinoic acid | 10$^{-10}$ | 100 | 9 × 10$^{-12}$ |
| | 10$^{-11}$ | 53.8 | |
| | 12$^{-12}$ | 23.1 | |
| (X = O, R = C₂H₅) | 10$^{-9}$ | 100 | 1 × 10$^{-10}$ |
| | 10$^{-10}$ | 50.0 | |
| | 10$^{-11}$ | 28.2 | |
| trans-retinoic acid | 10$^{-10}$ | 83.3 | 1 × 10$^{-11}$ |
| | 10$^{-11}$ | 50.0 | |
| | 10$^{-12}$ | 16.7 | |
| (X = S→O, R = C₂H₅) | 10$^{-8}$ | 71.4 | 6 × 10$^{-10}$ |
| | 10$^{-9}$ | 71.4 | |
| | 10$^{-10}$ | 18.6 | |
| trans-retinoic acid | 10$^{-10}$ | 83.7 | 1 × 10$^{-10}$ |
| | 11$^{-11}$ | 50.0 | |
| | 10$^{-12}$ | 33.3 | |
| (X = O, R = H) | 10$^{-8}$ | 100 | 2 × 10$^{-10}$ |
| | 10$^{-9}$ | 100 | |
| | 10$^{-10}$ | 57.1 | |
| | 10$^{-11}$ | 11.14 | |

$^a$ED$_{50}$(M) is the dose for reversal of keratinization in epithelium of 50% of retinoid-deficient hamster tracheas in organ culture.

EXAMPLE VII 2-(2-Methoxy-5-bromophenyl)-2-methyl-1-chloropropane (20)

Concentrated H₂SO₄ (4 mL, 7.6 g, 0.077 mol) was added dropwise under N₂ to stirred 4-bromoanisole (44.0 g, 0.235 mol). After warming the mixture to 36° C. (warm water bath), distilled B-methallyl chloride (21.5 mL, 20.0 g, 0.221 mol) was added dropwise to the stirred mixture in 4 equal portions over a period of 1.6 hours (4×0.4 h). During the addition of the B-methallyl chloride, the temperature of the mixture was maintained at 35°-44° C. (using a warm water bath). After the addition of the B-methally chloride was complete (1.6 h), the reaction mixture became solid and was allowed to stand [1 hour over water bath (29°-32° C.), 2 hours at room temperature]. The wet solid was partitioned between H₂CCl₂ (500 mL) and H₂O (175 mL). The organic layer was separated and then washed with 5% aqueous NaHCO₃ (175 mL) and H₂O [175 mL, 5 mL of brine being added to destroy an emulsion which formed]. After drying (MgSO₄, 36 h), the organic solution, the solvent was removed, and the solid residue was vacuum distilled to remove a lower boiling liquid (bp 42% 0.15 mm-95° C./0.07 mm, mostly 4-bromoanisole). A solution of the remaining solid residue in H₂CCl₂ was treated with decolorizing charcoal. Evaporation of the H₂CCl₂ gave a tan solid which was recrystallized (twice, heptane) and dried [traces of solvent were removed (high vacuum)] to give the aryl ether as a white crystalline solid (37.7 g, 61.5%); mp 87.8°-89.1° C. [literature reports 82°-84° C.; see P. Gates, D. Baldwin, C. A. Wilson and J. Gillion (Fison's Ltd.), U.S. Pat. No. 4,333,759; Chem Abstr. 1982, 97, 215978 p]. Another 3.4 g (5.5%) could be obtained by the following procedure. Evaporation of the mother liquors gave a solid which was dissolved in H₂CCl₂. Partial decolorization (charcoal) of the H₂CCl₂ solution followed by evaporation gave a solid residue which was recrystallized (twice, heptane); the yield of ether was 41.1 g (67%). IR(KBr) 1246 cm$^{-1}$ (C—O); $^1$H NMR (DCCl₃) δ1.43 [s, 6H, C(CH₃)], 3.96 (s, 2H, OCH₂), 6.78 (d, 1H, Ar—H), 7.32-7.41 (m, 2H, Ar—H); $^{13}$C NMR (DCCl₃) ppm 25.8 [C(CH₃)₂], 40.4 [C(CH₃)₂], 53.3 [CH₂C], 55.3 [OCH₃]; Ar—C [113.1, 130.6, 131.2, 135.4, 157.2] Both hydrogen and carbon-13 NMR spectral shifts were measured from tetramethylsilane (TMS on a Varian XL-300 NMR spectrometer confirming the correct hydrogen distribution and carbon atoms assignments.

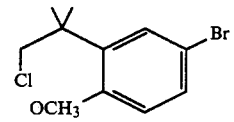

(20)

EXAMPLE VIII

5-Bromo-2.3-dihydro-3.3-dimethylbenzofuran (21)

A mixture of 2-(2-methoxy-5-bromophenyl)-2-methyl-1-chloropropane (ether above; 12.60 g 0.045 mol), pyridine hydrochloride (23.7 g 0.205 mol), and quinoline (22.9 g 0.177 mol) was heated to 164° C. (boiling isobutylbenzene bath) under N₂ with stirring over a period of 0.6 hours. After stirring a reflux (164°-167° C.) for 3 hours, the mixture was partitioned between ice-cold 6N HCl (225 mL). The organic layer was separated and the aqueous layer was extracted (ether 200 mL). After drying (MgSO₄, overnight) the combined organics, the solvent was evaporated and the residual oil was vacuum distilled to give the cyclic ether (8.5 g, 82%) as a colorless liquid: bp 48.2°-60.0° C./0.05-0.06 mm [literature reports 62°-64° C./0.01 mm; see P Gates, D. Baldwin, C. A. Wilson, and J. Gillon (Fison'Ltd.), U.S. Pat. No. 4,333,759; Chem. Abstr. 1982, 97, 215978 p)]. TLC analysis [1:5 ethyl acetate:petroleum ether (bp 50°-110° C.)] indicated traces of two impurties. IR(neat) 1197 cm$^{-1}$ (C—O); $^1$H NMR (DCCl₃) δ1.31 [2, 6H, C(CH)₂], 4.24 (s, 2H, OCH₂), 6.67 (D, 1H, Ar—H), 7.18-7.25 (m, 2H, Ar—H); $^{13}$C NMR (DCCl₃) ppm 27.3 [C[CH₃)₂] 84.7 [OCH₂]; Ar—C [111.2, 112.2, 125.4, 130.6, 138.9 158.2].

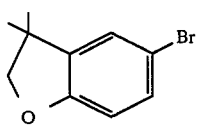   (21)

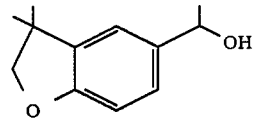   (22)

EXAMPLE IX 1-(2,3-Diydro-3,3-dimethyl-5-benzofuranyl)ethanol (22)

A mixture of the precursor ether (0.21 g. 0.9 mmol), Mg turnings (1.0 g 0.041 g at) and dry THF (2 mL) was heated (heat gun) under $N_2$ until the mixture turned cloudy (ca 15 min). Dry THF (15 mL) was added to the mixture which was then heated to reflux. A solution of ether 21 (2.92 g, 12.9 mmol) in dry THF (25 mL) was added dropwise to the vigorously stirred mixture over a period of 0.75 hours. After vigorous stirring at reflux for 2.75 hours, another 0.25 g (0.010 g at) of Mg turnings were added. The new mixture was stirred at reflux for 0.75 hour and with no external heat for 0.5 hours. Upon cooling the mixture to $-5°$ to $-10°$ C. (ice-salt bath), a solution of freshly distilled acetaldehyde (2.0 g, 0.045 mol) in dry THF (20 mL) was added dropwise to the vigorously stirred mixture over a period of 0.7 hours. This reaction mixture was stirred in an ice-salt bath ($-5°$ to $-10°$ C.) for 1.5 hours, after which time a solution of acetaldehyde (0.9 g, 0.020 mol) in dry THF (5 mL) was added dropwise (over a period of about 0.2 h) and the new mixture was stirred 0.3 hours. With continued cooling ($-5°$ to $-10°$ C.), saturated aqueous $NH_4Cl$ (3 mL) was added and the excess Mg turnings were removed by filtration. Saturated aqueous $NH_4Cl$ (10 mL) and ether rinses (of glassware and Mg turnings, 60 mL) were added to the filtrate. After separating the organic layer, the aqueous phase (pH>8) was acidified (pH 6.5 to 7) with saturated aqueous $NH_4Cl$ (15 mL) and 4% $H_2SO_4$ (14 mL). The aqueous solution was extracted with ether (5×40 mL) and ether (90 mL) was added to the combined organics. The organic solution was washed with saturated aqueous $NaHCO_3$ (75 mL) and brine (50 mL). After drying ($MgSO_4$) the solution, the solvent was removed, and the residual oil was chromatographed through a circular silica gel plate (4 mm) spun by a Chromatotron (Model 7924T, Harrison Research, 840 Moana Court, Palo Alto, Calif. Half of the product was eluted with ether/petroleum ether (bp 50°-110° C.) 20:1, 8:1, then 4:1 and then the same solvent system was used to elute the other half. In both separations, the 4:1 ratio was required to elute the title compound. Concentration of the eluent in the desired fractions gave 1.18 g (44%) of the alcohol as a light yellow, viscous oil. TLC analysis (1:4 ether:petroleum ether, bp 50°-110° C.) indicated the compound was essentially pure.

IR (neat) 3150-3650 $cm^{-1}$; $^1H$ NMR ($DCCl_3$) $\delta$1.31 [s, 3H, $C(CH_3)CH_3$], 1.32 [s, 3H, $C(CH_3)CH_3$], 1.45 [d, 3H, $CH(CH_3)$], 2.36 (bs, 1H, O—H), 4.81 [q, 1H, $CH(CH_3)$], 6.71 [d, J=8 Hz, 1H, H(7)], 7.08 [dd, J=8 Hz, J=1.9 Hz, 1H, H(6)], 7.13 [d, J=1.9 Hz, 1H, H[4)]; $^{13}C$ NMR ($DCCl_3$) ppm 25.1 [$CH(CH_3)$], 27.5 [$C(CH_3)_2$], 41.9 [$C(CH_3)_2$, 7.02 [C—OH], 84.7 [$OCH_2$]; Ar—C [109.3, 119.5, 125.4, 136.8, 138.3, 158.6].

EXAMPLE X

[1-(2,3-Dihydro-3,3-dimethyl-5-benzofuranyl)ethyl]triphenylphosphonium Bromide (23)

A solution of the precursor alcohol 22 (0.28 g, 1.46 mmol) in methanol (5 mL) was added dropwise (about 3 min.) under $N_2$ to a stirred mixture of triphenylphosphine hydrobromide (0.50 g, 1.46 mmol) in methanol (10 mL). After 7 min, the mixture became a solution which was stirred at room temperature for 40 hours. Evaporation of the solvent resulted in foaming and gave a colorless solid. The solid was changed to a powder by stirring the suspension of crude 23 in ether for 4.5 hours. After filtering the solid, the fine powder was partially dried (air) and finally dried by high vacuum ($P_2O_5$, 100° C.), to give 0.69 g (88%) of the phosphonium salt as a creamy white powder; mp 207°-212° C.; $^1H$ NMR ($DCCl_3$) $\delta$1.14 [s, 3H, $(CH_3)CCH_3$], 1.19 [S, 3H, $(CH_3)CCH_3$], 1.82 (dd, 3H, $CHCH_3$), 4.22 (s, 2H, $OCH_2$), 6.56 (m, 1H, $CHCH_3$), 6.61 (d, 1H, Ar—H), 6.85-6.98 (m, 2H, Ar—H), 7.64-7.92 [m, 15H, $P(C_6H_5)_3$]. The salt was used without further purification.

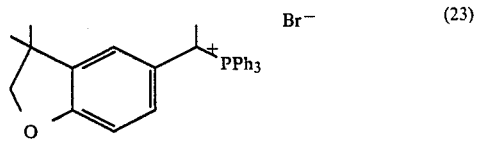   (23)

EXAMPLE XI

Methyl (E)-p-[2-(2,3-Dihydro-3,3-dimethyl-5-benzofuranyl)-propenyl]benzoate or Methyl (E)-4-[2-(2,3-Dihydro-3,3-dimethyl-5-benzofuranyl)-1-propenyl]benzoate (24)

A solution of -n-butyllithium (1.38M, 2.0 mL, 2.76 mmol) in hexane was added dropwise (about 3 minutes) under $N_2$ to a stirred suspension of the precursor phosphonium salt 23 (1.45 g, 2.72 mmol) in dry ether (20 mL). The resulting red mixture was stirred at room temperature (0.2 hours). After cooling the mixture in a dry ice-acetone bath (78° C, 0.2 hours) a solution of aldehyde 33 (0.45 g, 2.74 mmol) in dry ether (20 mL) was added dropwise over a period of 1 minute. The mixture became cream-colored and a large amount of creamy-white solid precipitated. After stirring at room temperature 54 hours, ether (75 mL) was added to the mixture. The mixture was filtered and the solid was washed with ether (140 mL). The filtrates were combined and the solvent was evaporated leaving a yellow oil which was chromatographed through a circular silica gel plate (4 mm) spun by a Chromatotron (Model 7924T, Harrison Research, 840 Moana Court, Palo Alto, Calif). The product was eluted with 1:9 ethyl acetate:hexanes (200 mL). Fraction 2 and 3 were set aside; fractions 4-10 were combined and evaporated to about 2 mL. This solution was chromatographed as described above and fractions 2' and 3' were combined with 2 and 3. Evaporation of the solvent gave an oil which solidified. Recrystallization (minimum amount of hot 95% ethanol) gave, after drying (P$_2$O$_5$, high vacuum, 61° C.), 1.88 mg (21.4%) of E-ester 24 as colorless flakes: mp 100.3°-100.8° C.; IR (KBr) 1717 cm$^{-1}$ (C=O); $^1$H NMR (DCCl$_3$) 1.38 [s, 6H, C(CH$_3$)$_2$], 2.29 [d, J=1.2 Hz, 3H, CH=C(CH$_3$)], 3.93 (s, 3H, OCH$_3$), 4.28 (s, 2H, OCH$_2$), 6.77 [bs, 1H, CH=C(CH$_3$)], 6.80 [d, J=8.3 Hz, 1H, H(7)], 7.28 [d, J=2 Hz, 1H, H(4)], 7.31 [dd, J=8.3 Hz, J=2 Hz, 1H, H(6)], 7.41 (d, 2H, Ar—H), 8.03 (d, 2H, Ar—H); $^{13}$C NMR (DCCl$_3$) ppm 17.9 [CH=C(CH$_3$)], 27.6 [(CH$_3$)$_2$C], 41.9 [(CH$_3$)$_2$C], 52.0 [OCH$_3$], 84.9 [OCH$_2$]; Ar—C [109.3, 120.0, 125.1, 126.1, 127.6, 129.0, 129.4, 136.4, 136.8, 139.6, 143.4, 159.0], 167 [C=O]; Anal. Calcd for C$_{21}$H$_{22}$O$^3$: C, 78.23; H, 6.88. Found D, 77.88; H, 6.98. Evaporation of the solvent from the mother liquors and recrystallization (hot 95% ethanol) of the residue gave needles and diamond-shaped crystals. Manual separation of the crystals and recrystallization (hot 95% ethanol) of each gave another 23 mg (2.6%) of E-ester 24 as colorless, diamond-shaped crystals and needles of Z-ester 25 (18 mg, 2%) were also obtained: mp 103.0°-104.2° C.; $^1$H NMR (DCCl$_3$) δ1.21 [s, 6H, C(CH$_3$)$_2$], 2.22 [d, J=1.3 Hz, 3H, CH=C(CH$_3$)], 3.87 (s, 3H, OCH$_3$), 4.24 (s, 2H, OCH$_2$), 6.43 [bs, 1H, CH=C(CH$_3$)], 6.71 [d, J=8.2 Hz, 1H, H(7)], 6.84 [d, J=1.7 Hz, 1H, H(4)], 6.96 [dd, J=8.2 Hz, J=1.7 Hz, 1H, H(6)], 7.02 (d, 2H, Ar—H), 7.77 (d, 2H, Ar—H); $^{13}$C NMR (DCCl$_3$) ppm 27.1 [CH=C(CH$_3$)], 27.4 [(CH$_3$)$_2$C], 41.8 [(CH$_3$)$_2$C), 51.9 [OCH$_3$], 84.7 [OCH$_2$]; Ar—C (109.6, 122.6, 125.1, 127.3, 127.7, 128.8, 129.1, 133.6, 136.8, 141.6, 142.9, 158.6] 167.0 [C=O].

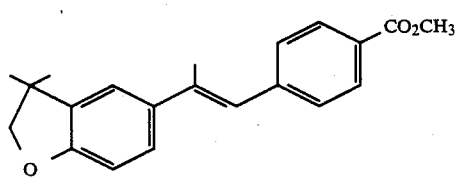

(24)

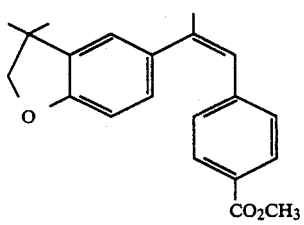

(25)

EXAMPLE XII (E)-p-[2-(2,3-Dihydro-3,3-dimethyl-5-benzofuranyl)-propenyl]benzoic acid or (E)-4-[2-(2,3-Dihydro-3,3-dimethyl-5-benzofuranyl)-1-propenyl]benzoic acid (26)

The E-isomer of heteroarotinoid 24 (R=CH$_3$) (90 mg, 0.28 mmol) was heated at reflux under N$_2$ for 5 hours in a solution of NaOH (0.06 g, 1.5 mmol) in 95% C$_2$H$_5$OH (1.2 mL) and H$_2$O (3 mL). After cooling slowly to a few degrees above room temperature, the solution was acidified (litmus) with 6N HCl. A white solid formed and was filtered, washed (H$_2$O, about 5 ml) and recrystallized (hot 95% ethanol) to give 38 mg (44%) of E-acid 26 as white crystals: mp 197.3°-198.5° C.; $^1$H NMR (DCCl$_3$) δ1.39 [s, 6H, (CH$_3$)$_2$C], 2.30 [d, J=1 Hz, 3H, CH=C(CH$_3$)], 4.28 (s, 2H, OCH$_2$), 6.78–6.83 [m, 2H, CH=C(CH$_3$) and H(7)], 7.29 [d, J=2 Hz, 1H, H(4)], 7.32 [dd, J=8.2 Hz, J=2 Hz, 1H, H(6)], 7.46 (d, 2H, Ar—H), 8.12 (d, 2H, Ar—H) $^{13}$C NMR (DCCl$_3$) ppm 18.0 [CH=C(CH$_3$)], 27.6 [(CH$_3$)$_2$C], 41.9 [(CH$_3$)$_2$C], 84.9 [OCH$_2$]; AR—C [109.4, 120.0, 125.1, 126.1, 126.7, 129.1, 130.1, 136.4, 136.8, 140.0, 144.3, 159.1], 171.7 (C=O). Anal. Calcd. for C$_{20}$H$_{20}$O$_3$; C, 77.90; H, 6.54. Found: C, 77.20; H, 6.48.

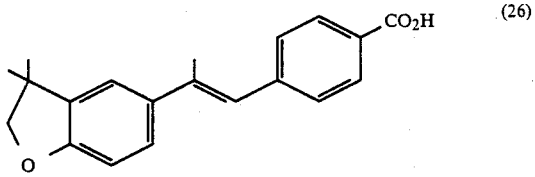

(26)

EXAMPLE XIII 4,4-Dimethylchroman or 3,4-dihydro-4,4-dimethyl-2-H-1-benzopyran (27)

A solution of 2-methyl-4-phenoxy 2-butanol (6.1 g, 33.62 mmol) in nitromethane (40 mL) was added dropwise under N$_2$ to a stirred suspension of anhydrous AlCl$_3$ (6.1 g, 45.35 mmol) in nitromethane (24 mL). After stirring at room temperature for an additional 24 hours, a solution of 6M HCl (65 mL) was added slowly. The resulting mixture was stirred for 10 minutes and diluted with ether (50 mL). The layers were separated, and the organic layer was washed with H$_2$O (50 mL), saturated NaHCO$_3$ (4×50 mL), H$_2$O (50 mL), and saturated solution of NaCl (2×50 ml). After the solution was dried (MgSO$_4$, 30 minutes), the solvent was removed (vacuum). Vacuum distillation of resulting dark brown oil gave 3.45 g (62.8%) of the pyran 27 as a colorless liquid: bp 38°-42° C./0.05 mm [literature reports 93° C./10 mm; see J. Colonge, E. Le Sech, and R. Marey Bull. Soc. Chim. France, 776 (1957)]; $^1$H NMR (DCCl$_3$) δ1.27 [s, 6H, (CH$_3$)C], 1.83 [m, 2H, CH$_2$], 6.88–7.24 [m, 4H, Ar—H]; $^{13}$C NMR (DCCl$_3$) ppm 30.5 [C(CH$_3$)$_2$], 31.1 [CH$_3$)$_2$C], 37.7 [CH$_2$], 63.0 [OCH$_2$], Ar—C [116.9, 120.4, 126.9, 127.0, 131.6, 153.6].

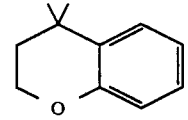

(27)

EXAMPLE XIV 4,4-Dimethylchroman-6-yl Methyl Ketone or 1-(3,4-Dihydro-4,4-dimethyl-2H-1-benzopyran-6-yl)ethanone (28)

Anhydrous AlCl$_3$ (2.99 g, 22.51 mmol) was added in small portions to 4,4-dimethylchroman (3.45 g, 21.30 mmol) and acetyl chloride (1.51 mL, 21.30 mmol) in CH$_3$NO$_2$ (30 mL) under N$_2$. After stirring at room temperature for 6 hours, 6M HCl (30 mL) was added slowly, and the resulting mixture was stirred for 10 minutes. The mixture was diluted with ether (70 mL) and the layers were separated. The organic layer washed with H$_2$O (50 mL), saturated aqueous NaHCO$_3$ (4×40 mL), H$_2$O (50 mL), and saturated solution of NaCl (50 mL). After the solution was dried (MgSO$_4$, 30 minutes) the solvent was removed to leave a dark, reddish brown oil. Vacuum distillation gave 3.09 g (89.03%) of the ketone 28 as a pale yellow liquid: bp 94°-95° C./0.1 mm [literature reports 108°-112° C./0.01 mm; see K. M. Waugh, K. D. Berlin, W. T. Ford, E. M. Holt, J. P. Carrol, P. R. schomber, M. D. Thompson, and L. J. Schiff *J. Med. Chem.*, 28, 116 (1985)]; IR (neat) 1675-1685 cm$^{-1}$ (C=O); $^1$H NMR (DCCl$_3$) δ1.38 [s, 6H, (CH$_3$)$_2$C], 1.84 [m, 2H, CH$_2$], 2.52 [s, 3H, CH$_3$C], 4.26 [m 2H, CH$_2$O], 6.82 [d, 1H, H(8)], 7.71 [dd, 1H, H(7)], 7.99 [d, 1H, H(5)]; $^{13}$C NMR (DCCl$_3$) ppm 26.1 [CH$_3$], 30.5 [C(CH$_3$)$_2$], 30.6 [CCH$_3$)$_2$C], 37.0 [CH$_2$], 63.3 [CH$_2$O], 116.7 [C$_8$], 127.5 [C$_5$], 127.9 [C$_7$], 130.0, 131.6 [C(4a), C$_6$], 157.8 [C(8a)], 196.4 [C=O].

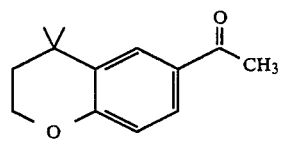

(28)

EXAMPLE XV

4,4-Trimethylchroman-6-methanol or 3,4-Dihydro-4,4-trimethyl-2H-1-benzopyran-6-methanol (29)

A solution of the methyl ketone 28 (2.12 g, 10.38 mmol) in anhydrous ether (10 mL) was added dropwise under N$_2$ to a stirred suspension of LiAlH$_4$ (0.59 g, 15.57 mmol) in dry ether (38 mL). The mixture was heated at reflux for 24 hours. After cooling to room temperature, ethyl acetate was added dropwise to destroy the excess LiAlH$_4$. A solution of 5% HCl (30 mL) was then added, and the resulting mixture was stirred for 5 minutes. The layers were separated, and the aqueous layer was washed (ether 2×50 mL). The combined organic layers were washed with 5% aqueous Na$_2$CO$_3$ (2×50 mL) and water (50 mL). After the solution was dried (MgSO$_4$, 30 minutes) the solvent was removed leaving a yellow oil which solidified after scratching. Recrystallization (hexane) gave 1.48 g 70.0% of the alcohol as a white solid: mp 71°-72° C. [literature reports 70°-71° C.; see K. M. Waugh, K. D. Berlin, W. T. Ford, E. M. Holt, J. P. Carrol, P. R. Schomber, M. D. Thompson, and L. J. Schiff *J. Med. Chem* 28, 116 (1985)]; IR (KBr) 3140-3640 CM$^{-1}$ (OH); $^1$H NMR (DCCl$_3$) δ1.32 [s, 6H, (CH$_3$)$_2$C], 1.50 [d, 3H, CH$_3$], 1.31 [s, 1H, OH], 4.20 [m, 2H, H(2)], 4.84 [q, 1H, CHOH], 6.76 [d, 1H, H(8)], 7.07 [dd, 1H, H(7)], 7.28 [d, 1H, H(5)]; $^{13}$C NMR (DCCl$_3$) ppm 24.9 [CH$_3$], 3.06 [C(4)], 31.0 [(CH$_3$)$_2$C], 37.6 [C(3)], 62.9 [C(2)], 70.2 [C(9)], 116.8 [C(8)], 123.9, 124.2 [C(5), C(7)], 131.1, 137.6 [C(4a), C(6)], 152.9 [C(8a)].

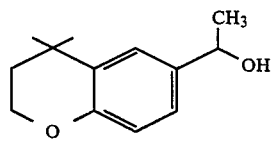

(29)

EXAMPLE XVI

[1-4,4-Dimethylchroman-6-yl)ethyl]triphenylphosphonium Bromide or [1-(3,4-Dihydro-4,4-dimethyl-2H-1-benzopyran-6-yl)ethyl]triphenylphosphonium Bromide (30)

A solution of the alcohol precursor 29 (0.70 g, 3.4 mmol) and triphenylphosphine hydrobromide (1.2 g, 3.5 mmol) in methanol (30 mL) was stirred under N$_2$ at room temperature for 24 hours. The solvent was removed (vacuum), and the resulting oil was triturated repeatedly with dry ether until it solidified. The white solid was suspended and stirred in dry ether (30 mL) at room temperature under N$_2$ for 4 hours, filtered, and dried (110° C./82 mm) to give 1.75 g (96.9%) of the salt as a white powder: mp 152°-156° C. (dec) [literature reports 149°-155° C.; see K. M. Waugh, K. D. Berlin, W. T. Ford, E. M. Holt, J. P. Carrol, P. R. Schomber, M. D. Thompson, and L. J. Schiff *J. Med. Chem*, 28, 116 (1985)]; $^1$H NMR (DCCl$_3$) δ1.08 [s, 3H, CH$_3$], 1.14 [s, 3H, CH$_3$], 1.76 [m, 2H, H(3)], 1.83 [d, 3H, CHCH$_3$], 4.16 [m, 2H, H(2)], 6.3 [m, 1H, CHP+Ph$_3$·Br$^-$], 6.57 [d, 1H, H(8)], 6.67 [d, 1H, H(7)], 7.74 [brs, 1H, H(5)], 7.63-7.84 [m, 15H, P+(C$_6$H$_5$)$_3$]. The salt was used without further purification.

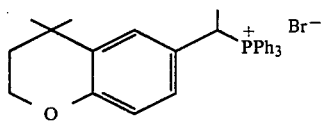

(30)

EXAMPLE XVII

Methyl (E)-4-[2-(3,4-Dihydro-4,4-dimethyl-2-H-1-benzopyran-6-yl)-1-propenyl]benzoate (31) and the Z-Isomer (32)

A solution of n-butyllithium in hexane (1.39M, 16.35 mL, 22.56 mmol) was added dropwise under N$_2$ to a stirred suspension of the precursor phosphonium salt (8.0 g, 15.04 mmol) in dry ether (145 mL). The resulting dark reddish brown mixture was cooled to 78° C., and a solution of methyl 4-formylbenzoate (2.47 g, 15.04 mmol) was added over a period of 3 minutes. The solution was stirred for a few minutes at −78° C. and then at room temperature for 48 hours. The mixture changed from reddish-brown to an off white color. After 48 hours, the reaction mixture was filtered. The resulting solid was washed with 350 mL of ether (anhydrous); the filtrate was concentrated to a yellow oil. This yellow oil was refrigerated for 8 hours and became a yellow solid. This yellow solid was passed through 30 g of silica gel (column, 8×200 mm). The product was eluted with 500 mL of hexane: ethyl acetate (4:1). Concentration of the eluent gave a viscous oil from which solid was obtained at room temperature. The white solid was dissolved in a minimum amount of boiling 95% ethanol and filtered hot. After the filtrate was concentrated, cooling this solution to room temperature gave 1.82 g of white crystals (35%): mp 90°-90.5° C.; IR (KBr) 1710-1725 cm$^{-1}$ (C=O); $^1$H NMR (DCCl$_3$) 1.4 [s, 6H, H(9), H(10)], 1.9 [m, 2H, H(3)], 2.3 [s, 3H, H(12)], 3.9 [s, 3H, H(21)], 4.2 [m, 2H, H(2)], 6.8 [ps, 1H, H(13)], 6.84 [d, 1H, H(8)], 7.3 [dd, 1H, H(7)], 7.4 [d, 1H, H(5)], 7.5 [d, 2H, H(15), H(19)], 8.6 [d, 2H, H(16) H(18)]; $^{13}$C NMR (DCCl$_3$) ppm 17.8 [C(12)], 30.7 [C(4)], 31.1 [C(9), C(10)], 37.6 [C(3)], 52.1 [C(21)], 63.1 [C(2)], 116.8 [C(8)], 124.5 [C(5)], 124.9 [C(7)], 125.9 [C(13)], 129.0 [C(15), C(19)], 129.5 [C(16), C(18)], 167.0 [C(20)], non-protonated and vinylic carbons (127.6, 131.3, 135.7, 139.5, 143.4, 153.4); mass spectral data for C$_{22}$H$_{24}$O$_3$: m/e (M+) 336.1725; found 336.1728. The mother liquor from the crystallization of the E-isomer 31 contained predominantly the Z-isomer 32 (105 mg, 2.0%) as a white needles: mp 80°-80.5° C.; $^1$H NMR (DCCl$_3$) δ1.12 [s, 6H, H(9), H(10)], 1.78 [m, 2H, H(3)], 2.20 [s, 3H, H(12)], 3.86 [s, 3H, H(21)], 4.17 [m, 2H, H(2)], 6.43 [s, 1H, H(13)], 6.73 [d, 1H, H(8)], 6.95 [dd, 1H, H(7)], 7.03 [d, 1H, H(5)], 7.51 [d, 2H, H(15), H(19)], 7.78 [d, 2H, H(16), H(18)]; $^{13}$C NMR (DCCl$_3$) ppm 26.79 [C(12)], 30.42 [C(4)], 30.78 [C(9), C(10)], 37.48 [C(3)], 51.91 [C(21)], 63.08 [C(2)], 116.9 [C(8)], 125.0 [C(5)], 126.5 [C(7)], 126.5 [C(13)], 129.1 [C(15)], [C(19)], 131.5 [C(16), C(18)], 167.0 [C(20)], non-protonated and vinylic carbons (127.5, 128.8, 128.97, 132.9, 141.4, 143.1).

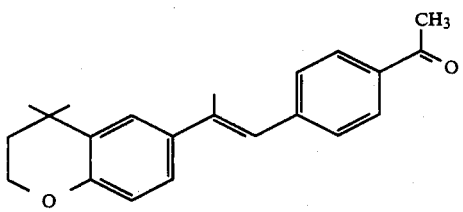

(31)

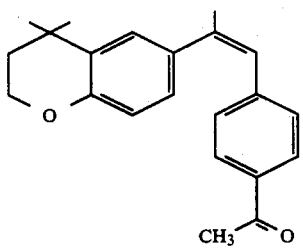

(32)

EXAMPLE XVIII

Methyl 4-Formylbenzoate (33)

A 500-mL, three-necked, round bottom flask was eqipped with a teflon-coated stirring bar, soxlet extractor and condensor with drying tube at the top. The flask was charged with 10.0 g (66.6 mmol) of 4-formylbenzoic acid, about 320 mL of absolute CH$_3$OH and 0.1 mL of concentrated H$_2$SO$_4$. The soxlet extractor was filled with 3 Å molecular sieve. After the solution was boiled for 48 hours, it was allowed to cool to room temperature and then was concentrated to a volume of about 50 mL, diluted with an equal amount of water, and extracted (ether 4×70 mL). The combined organic layers were washed with saturated NaHCO$_3$ solution (5×50 mL), 0.1 NHCl (10×40 mL), H$_2$O (2×50 mL), and saturated NaCl solution (2×50 mL). The resulting organic solution was finally dried (MgSO$_4$, 2 h) and filtered and concentrated in vacuo. The white solid obtained was recrystallized (hexane) to give 6.3 grams (57.6%) of ester 33 mp 59.5°-60° C. [literature reports 59°-60° C.; see J. M. Landesberg, M. A. Slam, and M. Mandel J. Org. Chem., 46, 5025 (1981)]; IR (KBr) 1680-1740 cm$^{-1}$ (C=O); $^1$H NMR (DCCl$_3$) δ4.00 (s, 3H, OCH$_3$), 7.80=8.32 (m, 4H, Ar-H), 10.10 (s, 1H, CHO); $^{13}$C NMR (DCCl$_3$)ppm 52.6 [OCH$_3$], Ar-C [129.6, 130.4, 135.2, 139.2], 166.0 [CO$_2$ CH$_3$], 191.7 [CHO]; mass spectral data for C$_9$H$_8$O$_3$: m/e (M+): 164.0473. Found: 164.0472.

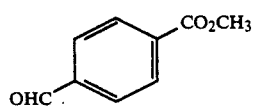

(33)

EXAMPLE XIX (E)-4-[2-Methyl-2-(4,4 dimethylchroman-6-yl]benxonitrile (34)

A solution of n-butyllithium in hexane (1.55M, 9.40 mmol, 6.15 mL) was added dropwise under N$_2$ to a stirred suspension of the precursor phosphonium salt 30 (5.00 g, 9.40 mmol) in dry ether (100 mL). The resulting dark, reddish brown mixture was cooled to −78° C. and this was added to a solution of 1.56 g (9.4 mmol) 4-cyanobenzaldehyde in 50 mL of anhydrous ether over a period of one minute. The solution was stirred for 2 minutes at −78° C. and at room temperature for two more hours. The mixture changed from a reddish brown to a pale yellow color. After 2 hours, the reaction mixture was filtered and the resulting solid was washed (anhydrous ether, 30 mL). The filtrate was concentrated to give a yellow oil. This yellow oil was kept overnight in refrigerator and yielded a yellow solid which was passed through 35 grams of silica gel [column, (8×200 mm)]. The product was eluted with 400 mL of hexane: ethylacetate (4:1); concentration of the eluent gave a viscous oil from which yellow solid was obtained at room temperature. The yellow solid was dissolved in a minimum amount of boiling absolute ethanol which gave fine pale yellow crystals [1.03 grams (35.1%)] of nitrile 34: mp 134°-134.5° C.; IR (KBr) 2220-2240 cm$^{-1}$ (CN); $^1$H NMR (DCCl$_3$) δ1.80 [s, 6H, (CH$_3$)$_2$C], 2.21 [s, 3H, CH$_3$—C], 2.30 [m, 2H, CH$_2$—C], 4.22 [m, 2H, CH$_2$—O], 6.33 [s, 1H, CH=C], 6.80 [d, 1H, H(8)], 7.21 [dd, 1H, H(7)], 7.44 [d, 1H, H(5)], 7.50 [d, 2H, H(15), H(19)], 7.90 [d, 2H, H(16), H(18)]; $^{13}$C NMR (DCCl$_3$) ppm 17.8 [C(12)], 30.7 [C(4)], 31.6 [C(9), C(10)], 35.6 [C(3)], 63.2 [C(2)], 116.9 [C(13)], 119.2 [C(20)], 124.3 [C(7)], 124.6 [C(5)], 124.9 [C(8)], 129.7 [C(16), C(18)], 131.9 [C(15), C(19)], non-protonated and vinylic carbons [109.4, 131.6, 135.3, 140.6, 153.6]; mass spectral data for C$_{21}$H$_{21}$NO: m/e (M+) 303.1623. Found: 303.1627.

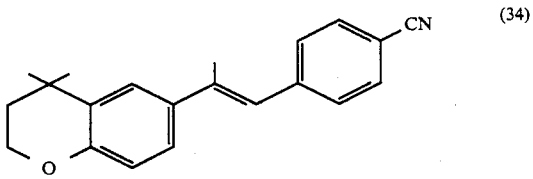

(34)

EXAMPLE XX (E)-4-[2-Methyl-2-(4,4-dimethyl-6-chromanyl)]benzyl Alcohol (35)

A solution of methyl (E)-4-[2-(3,4-dihydro-4,4-dimethyl-2H-1-benzopyran-6-yl)-1-propenyl]benzoate 31 (0.29 g, 0.86 mmol) in anhydrous tetrahydrofuran (2 mL) was added dropwise under N$_2$ to a stirred suspension of LiAlH$_4$ (0.04 g, 1.10 mmol) in dry THF. The mixture was heated at reflux for 8 hours and, after cooling to room temperature, ethyl acetate (8 mL) was added to destroy residual LiAlH$_4$. The resulting mixture was stirred for 5 minutes. The two layers were separated, and the aqueous layer was washed (ether, 2×25 mL). The combined organic layers were washed with 5% Na$_2$CO$_3$ (50 mL), H$_2$O (25 mL), and brine (25 mL). After drying (MgSo$_4$, 2 h), the organic solution was evaporated leaving a thick yellow oil. Chromatography using a Chromatotron with a silica gel plate (4 mm) and eluting with 80% hexane: ethyl acetate (200 mL total) gave, after concentration, a viscous oil which solidified after refrigeration overnight. Dissolving this solid in minimum amount of boiling hexane produced, after cooling, 65 mg (25%) of the alcohol 35 as a white amorphous powder; mp 79°–80° C. IR (KBr) 3510–3060 (O—H) cm$^{-1}$. $^1$H NMR (DCCl$_3$) $\delta$1.18 [s, 6H, (H$_3$C)$_2$C], 1.86 [m, 2H, H(3)], 1.90 [s, 1H, OH], 2.26 [s, 3H, H(12)], 4.22 [m, 2H, OCH$_2$CH$_3$], 4.70 [s, 2H, H(20)], 6.76 [s, 1H, CH=C(CH$_3$)], 6.82 [d, J=9 Hz, 1H, H(8)], 7.28 [dd, J=9 Hz, 1H, H(7)], 7.38 [s, 4H, H(15), H(16), H(18), H(19)], 7.44 [d, J=3 Hz, 1H, H(5)]. $^{13}$C NMR (DCCl$_3$) ppm 17.56 [C(12)], 30.70 [C(4)], 31—31 [C(9), C(10)], 37.66 [C(3)], 63.10 [C(2)], 65.18 [C(20)], 116.70 [C(8)], 124.40 [C(5)], 124.8 [C(7)], 125.37 [C(13)]. There are other non-protonated and vinyl carbons which could not be distinguished. 131.22, 136.02, 137.42, 138.70, 153.04: Mass spectral data for C$_{21}$H$_{24}$O$_2$: m/e (M+) 308.1776. Found: 308.1765.

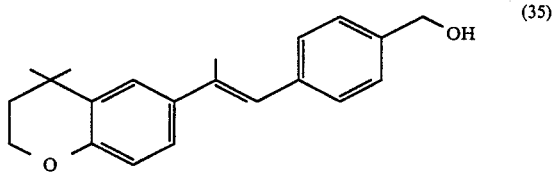

(35)

EXAMPLE XXI (E)-4-(2-Methyl-2-(4,4-dimethylchroman-6-yl)benzaldehyde (36)

A solution of nitrile 34 (0.200 g, 0.66 mmol) in 25 mL of dry ether under N$_2$ was stirred at room temperaure, and a solution of diisobutylaluminum hydride (DIBAL-H) in hexane (1.0M, 1.34 mL, 1.34 mmol) was added dropwise. When the addition was complete (2 min), the mixture was allowed to boil with stirring from 38 hours and was allowed to cool to room temperature. The resulting solution was diluted with CH$_3$OH (10 mL). Then dilute H$_2$SO$_4$ (5%, 25 mL) was added cautiously until the aqueous phase was acidic. This aqueous layer was washed with ether (2×25 mL). The combined organic phase and extract were washed with 5% NaHCO$_3$ (2×50 mL), water (50 mL), and finally with brine (25 mL). After drying (MgSO$_4$, 30 min), the solution was evaporated to a viscous yellow oil. Chromatography of the oil was performed using silica gel ($\simeq$12 grams) through a vertical column (8×200 mm). Elution was effected with hexane: ethyl acetate (4:1, 200 mL). Concentration of the eluent gave a viscous oil which solidified upon standing in an ice bath for 2 hours. Solution of the solid in a minimum amount of hot hexane gave, upon cooling, 51 mg (26% of aldehyde 36 as a white crystalline material: mp 85°–86° C. IR (KBr) 2750 (CH=O), 1700 (C=O) cm$^{-1}$; $^1$H NMR (DCCl$_3$) $\delta$1.39 [s, 6H, (H$_3$C)$_2$C]. 1.86 [m, 2H, H(3)], 2.29 [s, 3H, H(12)], 4.22 [m, 2H, OH$_2$CH$_3$], 6.77 [s, 1H, CH=CH$_3$], 6.81 [d, J=9 Hz, 1H, H(8)], 7.26 [dd, J=9 Hz, J=3 Hz, 1H, H(5)], 7.51 [d, J=9 Hz, 2H, H(15), H(17)], 7.87 [d, J=9 Hz, 2H, H(16), H(18)], 10.0 [s, 1H, CHO]; $^{13}$C NMR (DCCl$_3$) ppm 17.88 [C(12)], 30.7 [C(4)], 31.65 [C(9)C(10)], 37.60 [C(3)], 63.14 [C(2)], 116.8 [C(8)], 124.56 [C(5)], 124.93 [C(7)], 129.61 [C(13)], 191.79 [CHO], non-protonated and vinyl carbons: 129.67, 131–39, 134.14, 135.50, 140.39, 145.08, 153.39; mass spectral data for C$_{21}$H$_{22}$O$_2$ m/e (M+): 306.1619. Found: 306.1617.

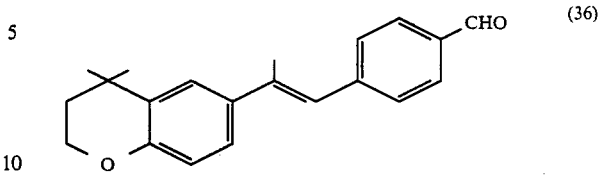

(36)

EXAMPLE XXII

In order to demonstrate and evaluate the biological activity of the heteroarotinoids according to the present invention, selected compounds were assayed either via analysis of the suppression of the 12-o-tetradeconoyl-phorbol-13-acetate (TPA) induced synthesis of ornithine decarboxylase (ODC) in mouse skin or the induction of differentiation of human (HL-60) promyelocytic cells. In the ODC assay, either 13-cis-retinoic acid or trans-retinoic acid was employed. The following Table summarizes the result of the ODC assays.

TABLE

| Heteroarotinoids Test System | Retinoid Dose, nmol | ODC Activity* | % of Inhibition as Compared to Control |
|---|---|---|---|
| Acetone | 0.0 | 0.00 ± 0.0 | — |
| Acetone + TPA[1] | 0.0 | 0.90 ± 0.31 | control |
| 13-cis-retinoic acid + TPA | 17 | 0.1 ± 0.01 | 89% |
| *nmol CO$_2$/30 min/mg protein | | | |
| Acetone | 0.0 | 0.00 ± 0.0 | — |
| Acetone + TPA | 0.0 | 1.67 ± 0.14 | Control |
| 13-cis-retinoic acid + TPA | 17 | 0.14 ± 0.04 | 92 |
| 31 + TPA | 34 | 0.95 ± 0.06 | 43 |
| 34 + TPA | 34 | 1.77 ± 0.32 | |
| Acetone | 0.0 | 0.00 ± 0.0 | — |
| Acetone + TPA | 0.0 | 5.3 ± 0.7 | Control |
| trans-retinoic acid + TPA | 34 | 1.0 ± 0.1 | 81 |
| 35 + TPA | 34 | 1.7 ± 0.1 | 68 |
| 36 + TPA | 34 | 3.5 ± 0.2 | 34 |
| 24 + TPA | 34 | 1.5 ± 0.4 | 72 |

*nmol CO$_2$/60 min/mg protein

TPA =

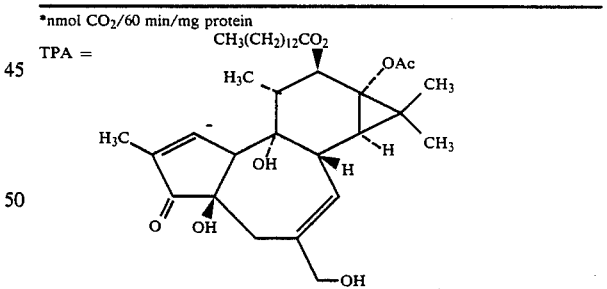

In the screening tests of the Table, the selected retinoids in 0.2 ml of acetone were applied 1 hour before the application of 10 nmole of TPA to the shaved backs of mice; the mice where then sacrificed for ODC assay 5 hours after TPA treatment. Epidermus was separated, homogenized, and centrifuged at 30,000×g. Soluble epidermal ODC activity was assayed. The retinoids were evaluated in three independent experiments (3 groups of mice with 3 mice per group) and the results from the experiments were normalized (% inhibition) for comparison. As seen from the data, the furanyl ester 24 had the strongest activity while the chromanyl alcohol 35, ester 31 and aldehyde 36, were less active in inhibiting ODC induction by TPA. Under the same conditions as used for the alcohol 24 and aldehyde 36, the furanyl ester 24 exhibited strong activity as compared to the control. In experiments with 13-cis-retinoic acid as the standard, the relative activities of the retinoids in suppressing TPA induction of ODC were: 13-cis-retinoic acid 31>34. In experiments with trans-retinoic acid as a standard, the relative activities were: trans-retinoic acid >24>35>36. Which standard is used appears to be relatively unimportant for determining activity in the assay, but the data presented in the Table identifies the standard for sake of clarity and accuracy of presentation. Thus, the presence of the heteroatom in these arotinoids has not eliminated biological activity. It is also clear that the acid in the simple esters are the most active regardless of whether sulfur or oxygen is the heteroatom. Consequently, the nature of the terminus group is also important.

EXAMPLE XXIII

In order to evaluate the efficacy of the heteroarotinoids to induce HL-60 cell differentiation along the granulocytic maturation pathway, HL-60 cells were grown in a serum-free medium consisting of HRPMI 1640 supplemented with 10 nM 4-(2-hydroxyethyl)-1-piperazineethane sulfonic acid, 5 μg of insulin/mL, and 5 μg of transferrin/mL. These mature cells, unlike the uninduced HL-60, produced superoxide anion when simulated with an appropriate agent, such as TPA. The ability of the individual cells to produce superoxide can be measured by incubating cells with the water-soluble yellow dye, nitroblue tetrazolium (NBT). NBT is reduced to a water-insoluble blue-black formazan by superoxide. This formazan precipitate is associated with those cells that produce superoxide. Thus, the percentage of cells in a population that produce superoxide (NBT-positive cells) can be enumerated under a light microscope.

The retinoids were dissolved in DMSO or ethanol and diluted into the culture medium so that the final concentration of the solvent did not exceed 0.1%, a concentration that has no effect on differentiation. After incubation for 4 days at 37° C. in a humidified atmosphere of 5% $CO_2$ and air, the capacity of the cells to reduce NBT was determined. Viable cells ($10^6$) were harvested by centrifugation and suspended in 0.5 mL of RPMI 1640 containing 20% fetal bovine serum. This cell suspension was mixed with an equal volume of phosphate buffered saline containing 1 mg of NBT/mL and 200 mg of TPA/mL. The reaction mixture was incubated at 37° C. for 25 minutes, and the reaction was terminated by cooling in an ice water bath. Cytospin slides were prepared from a portion of this reaction mixture and stained with Wright-Giemsa. A minimum of 200 cells were counted under light microscopy to determine the percentage of cells with cell-associated formazan.

The concentrations of retinoid effective in achieving a half-maximal response ($ED_{50}$) for the esters 31, 24, 35, and the free acid 26 and that derived from 34, were all greater than 3 μM. At a concentration of 3 μM, both 31 and acid derived from 34 induced approximately 15% of the cells to differentiate while 24 and 25 gave values of 3 to 5%, the same as the control. It has been reported previously that tetrahydrotetramethylnaphthalenylpropenylbenzoic acid (TTNPB) has an $ED_{50}$ of approximately 200 nM in the HL-60 differentiation assay. The findings in this study that acid derived from 34 has an $ED_{50}$ of <3,000 nM indicates that the substitution of an oxygen atom in the cyclohexyl ring of TTNPB is responsible for this decrease in activity,. In a related finding, substitution of a sulfur atom at the same position in the cyclohexyl ring of the TTNPB results in a large decrease in biological activity measured either as the effectiveness in reversing keratinization in tracheas from vitamin A-deficient hamsters or in competing with retinoic acid for sites on the cellular retinoic acid-binding protein from the same tissue. Because the acid derived from 34 and the sulfur-substituted TTNPB derivative have not been tested for biological activity in the same assay, the relative activity of these two retinoids is not known. However, based on the relative activities in the present study, it is likely that the oxygen-substituted derivative would have a lower biological activity than the sulfur-substituted derivative. Thus, it can be concluded that the heteroarotinoids examined display a range of activities in the ODC and HL-60 screens. The most significant activity was found in systems in which sulfur replaced the C(1) position in the cyclohexyl ring system, although the replacement by oxygen gave examples with only slightly less activity.

Having thus described and exemplified the preferred embodiments with a certain degree of particularity, it is manifest that many changes can be made within the details of operation, operating parameters, and steps for synthesizing and using the heteroarotinoids according to the present invention without departing from the spirit and scope of this invention. Therefore, it is to be understood that the invention is not limited to the embodiments set forth herein for purposes of exemplification, but is to be limited only by the scope of the attached claims, including the full range of equivalents to which each step thereof is entitled.

We claim:

1. A compound selected from the group characterized by the formulae:

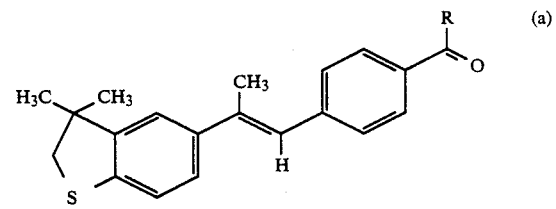

where R is H, OH, $OCH_3$, $OC_2H_5$ or

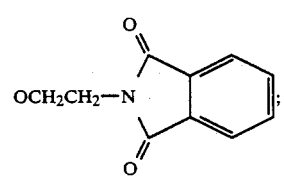

(b)
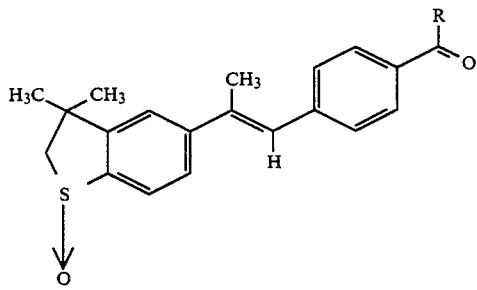

where R is H, OH, OCH₃, OC₂H₅ or

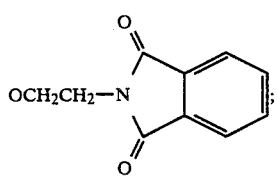

(c)
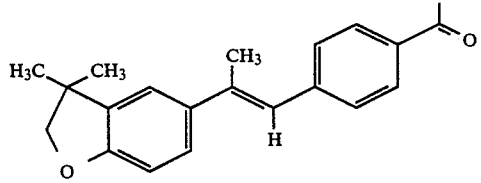

where R is H, OH, OCH₃, OC₂H₅ or

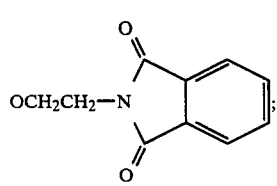

(d)
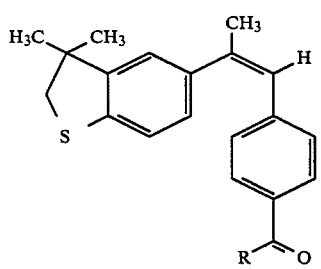

where R is H, OH, OCH₃, OC₂H₅ or

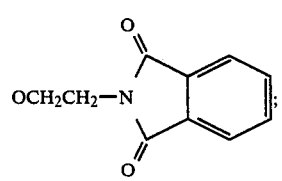

(e)
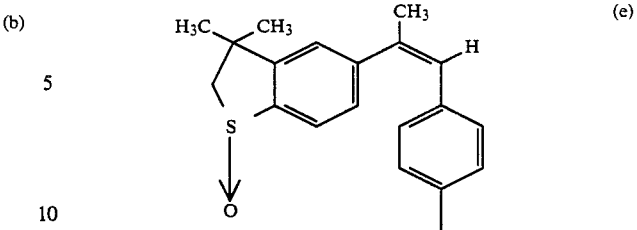

where R is H, OH, OCH₃, OC₂H₅ or

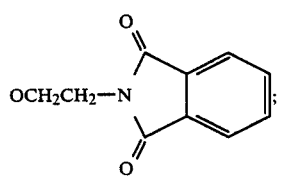

and (f)
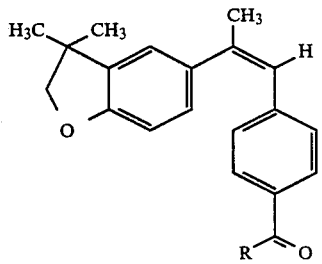

where R is H, OH, OCH₃, OC₂H₅ or

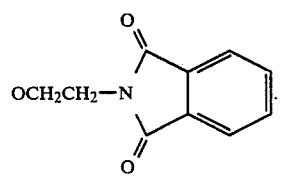

2. A compound selected from the group characterized by the formula:

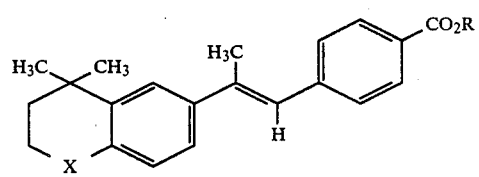

wherein X is selected from O, S, and S→O, and wherein R is selected from H, CH₃—, and C₂H₅.

3. A compound according to claim 2 consisting essentially of the trans isomer wherein X is S and R is C₂H₅.

4. A compound according to claim 2 consisting essentially of the trans isomer wherein X is O and R is C₂H₅.

5. A compound according to claim 2 consisting essentially of the trans isomer wherein X is S→O and R is C₂H₅.

6. A compound according to claim 2 consisting essentially of the trans isomer wherein X is O and R is H.

7. A compound selected from the group characterized by the formulas:

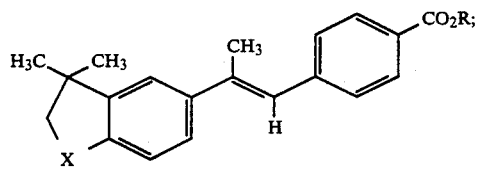

or

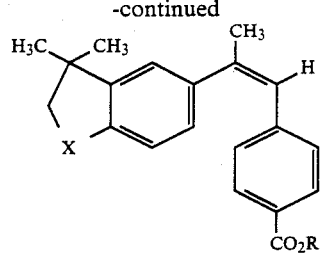

wherein X is selected from O, S, and S→O, and wherein R is selected from H, CH₃, and C₂H₅.

8. A compound according to claim 7 consisting essentially of the trans isomer wherein X is S and R is OH⁻ or OCH₃.

9. A compound according to claim 7 consisting essentially of the trans isomer wherein X is S→O and R is H or OCH₃.

10. A compound according to claim 7 consisting essentially of the trans isomer wherein X is O and R is OCH₃.

11. A compound according to claim 7 consisting essentially of the trans isomer wherein X is S and R is H.

12. A compound according to claim 7 consisting essentially of the trans isomer wherein X is S and R is OCH₃.

13. A compound according to claim 7 consisting essentially of the trans isomer wherein X is O and R is H.

* * * * *

UNITED STATES PATENT AND TRADEMARK OFFICE
CERTIFICATE OF CORRECTION

PATENT NO. : 4,826,984
DATED : May 2, 1989
INVENTOR(S) : BERLIN ET AL.

It is certified that error appears in the above—identified patent and that said Letters Patent is hereby corrected as shown below:

Col. 34, line 15, change "OH-" to --H---;
Col. 34, line 16, change "OCH$_3$" to --CH$_3$--;
Col. 34, line 19, change "OCH$_3$" to --CH$_3$--;
Col. 34, line 22, change "OCH$_3$" to --CH$_3$--;
Col. 34, line 27, change "OCH$_3$" to --CH$_3$--.

Signed and Sealed this

Twenty-third Day of April, 1991

*Attest:*

HARRY F. MANBECK, JR.

*Attesting Officer*     *Commissioner of Patents and Trademarks*